United States Patent [19]
Stimpson et al.

[11] Patent Number: 5,843,651
[45] Date of Patent: *Dec. 1, 1998

[54] LIGHT SCATTERING OPTICAL WAVEGUIDE METHOD FOR DETECTING SPECIFIC BINDING EVENTS

[75] Inventors: Donald Irvine Stimpson, Gurnee; Julian Gordon, Lake Bluff; Joanell V. Hoijer, Arlington Heights, all of Ill.

[73] Assignee: Abbott Laboratories, Abbott Park, Ill.

[ * ] Notice: The term of this patent shall not extend beyond the expiration date of Pat. No. 5,599,668.

[21] Appl. No.: 434,354

[22] Filed: May 2, 1995

Related U.S. Application Data

[62] Division of Ser. No. 311,462, Sep. 22, 1994, Pat. No. 5,599,668.

[51] Int. Cl.⁶ .............................. C12Q 1/68; C12Q 1/70; C07H 21/04; G01N 25/20
[52] U.S. Cl. .................... 435/6; 435/5; 536/24.3; 536/24.32; 536/24.33; 422/51; 385/130
[58] Field of Search .............................. 435/6, 5; 422/50, 422/51; 385/130; 536/24.3, 32, 33

[56] References Cited

U.S. PATENT DOCUMENTS 5,192,510   3/1993   Zoha et al. ............................ 422/82.05

FOREIGN PATENT DOCUMENTS

WO8909408   10/1989   WIPO .
WO9400763   1/1994   WIPO .

*Primary Examiner*—W. Gary Jones
*Assistant Examiner*—Dianne Rees
*Attorney, Agent, or Firm*—Thomas D. Brainard; Paul D. Yasger

[57] ABSTRACT

A waveguide binding assay method involves detecting the scattering of light directed into the waveguide, the scattering being the result of scattering labels specifically bound to the waveguide within the penetration depth of an evanescent wave. The waveguide may be transparent plastic or glass and the binding is typically by oligonucleotide hybridization or immunological capture. Light scattering labels include colloidal metals or non-metals, including gold, selenium and latex. A light absorbing member consisting of dye or concentrated particles may also be employed to enhance signal. Real-time binding and dissociation can be monitored visually or by video imaging, such as with a CCD camera and frame grabber software. Hybridization mismatches of as few as one base can be distinguished by real-time melting curves.

2 Claims, 13 Drawing Sheets t=0 (filling)

t=1 second t=5 seconds t=20 seconds

Air Bubbles

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: synthetic DNA ( i x ) FEATURE:
        ( A ) NAME/KEY: 3'amine
        ( B ) LOCATION: 15

( x i ) SEQUENCE DESCRIPTION: SEQ ID NO:1:

TATCATCTTT GGTGT 15

( 2 ) INFORMATION FOR SEQ ID NO:2:

( i ) SEQUENCE CHARACTERISTICS:
          ( A ) LENGTH: 15 base pairs
          ( B ) TYPE: nucleic acid
          ( C ) STRANDEDNESS: single
          ( D ) TOPOLOGY: linear ( i i ) MOLECULE TYPE: synthetic DNA ( i x ) FEATURE:
          ( A ) NAME/KEY: 3'amine
          ( B ) LOCATION: 15

( x i ) SEQUENCE DESCRIPTION: SEQ ID NO:2:

AATATCATTG GTGTT 15

( 2 ) INFORMATION FOR SEQ ID NO:3:

( i ) SEQUENCE CHARACTERISTICS:
          ( A ) LENGTH: 15 base pairs
          ( B ) TYPE: nucleic acid
          ( C ) STRANDEDNESS: single
          ( D ) TOPOLOGY: linear ( i i ) MOLECULE TYPE: synthetic DNA ( i x ) FEATURE:
          ( A ) NAME/KEY: 3'amine
          ( B ) LOCATION: 15

( x i ) SEQUENCE DESCRIPTION: SEQ ID NO:3:

AGTGGAGGTC AACGA 15

( 2 ) INFORMATION FOR SEQ ID NO:4:

( i ) SEQUENCE CHARACTERISTICS:
          ( A ) LENGTH: 15 base pairs
          ( B ) TYPE: nucleic acid
          ( C ) STRANDEDNESS: single
          ( D ) TOPOLOGY: linear ( i i ) MOLECULE TYPE: synthetic DNA ( i x ) FEATURE:
          ( A ) NAME/KEY: 3'amine
          ( B ) LOCATION: 15

( x i ) SEQUENCE DESCRIPTION: SEQ ID NO:4:

AGTGGAGATC AACGA 15

( 2 ) INFORMATION FOR SEQ ID NO:5:

( i ) SEQUENCE CHARACTERISTICS:
          ( A ) LENGTH: 15 base pairs
          ( B ) TYPE: nucleic acid
          ( C ) STRANDEDNESS: single
          ( D ) TOPOLOGY: linear ( i i ) MOLECULE TYPE: synthetic DNA ( i x ) FEATURE:
          ( A ) NAME/KEY: 3'amine
          ( B ) LOCATION: 15

( x i ) SEQUENCE DESCRIPTION: SEQ ID NO:5:

AGGTCAACGA GCAAG 15

( 2 ) INFORMATION FOR SEQ ID NO:6:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: synthetic DNA ( i x ) FEATURE:
    ( A ) NAME/KEY: 3'amine
    ( B ) LOCATION: 15

( x i ) SEQUENCE DESCRIPTION: SEQ ID NO:6:

AGGTCAATGA GCAAG 15

( 2 ) INFORMATION FOR SEQ ID NO:7:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: synthetic DNA ( i x ) FEATURE:
    ( A ) NAME/KEY: 3'amine
    ( B ) LOCATION: 15

( x i ) SEQUENCE DESCRIPTION: SEQ ID NO:7:

TGGAGATCAA TGAGC 15

( 2 ) INFORMATION FOR SEQ ID NO:8:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: synthetic DNA ( i x ) FEATURE:
    ( A ) NAME/KEY: 3'amine
    ( B ) LOCATION: 15

( x i ) SEQUENCE DESCRIPTION: SEQ ID NO:8:

TGGAGATCAA CGAGC 15

( 2 ) INFORMATION FOR SEQ ID NO:9:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: synthetic DNA ( i x ) FEATURE:
    ( A ) NAME/KEY: 3'amine
    ( B ) LOCATION: 15

( x i ) SEQUENCE DESCRIPTION: SEQ ID NO:9:

TGGAGGTCAA TGAGC 15

( 2 ) INFORMATION FOR SEQ ID NO:10:

( i ) SEQUENCE CHARACTERISTICS:
    ( A ) LENGTH: 15 base pairs
    ( B ) TYPE: nucleic acid (C) STRANDEDNESS: single
(D) TOPOLOGY: linear (ii) MOLECULE TYPE: synthetic DNA (ix) FEATURE:
(A) NAME/KEY: 3'biotin
(B) LOCATION: 15

(xi) SEQUENCE DESCRIPTION: SEQ ID NO:10:

ACACCAAAGA TGATA 15

(2) INFORMATION FOR SEQ ID NO:11:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: synthetic DNA (ix) FEATURE:
(A) NAME/KEY: 3'biotin
(B) LOCATION: 15

(xi) SEQUENCE DESCRIPTION: SEQ ID NO:11:

AACACCAATG ATATT 15

(2) INFORMATION FOR SEQ ID NO:12:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: synthetic DNA (ix) FEATURE:
(A) NAME/KEY: 3'biotin
(B) LOCATION: 15

(xi) SEQUENCE DESCRIPTION: SEQ ID NO:12:

TCGTTGACCT CCACT 15

(2) INFORMATION FOR SEQ ID NO:13:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: synthetic DNA (ix) FEATURE:
(A) NAME/KEY: 3'biotin
(B) LOCATION: 15

(xi) SEQUENCE DESCRIPTION: SEQ ID NO:13:

TCGTTGATCT CCACT 15

(2) INFORMATION FOR SEQ ID NO:14:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: synthetic DNA ( i x ) FEATURE:
   ( A ) NAME/KEY: 3'biotin
   ( B ) LOCATION: 15

( x i ) SEQUENCE DESCRIPTION: SEQ ID NO:14:

CTTGCTCGTT GACCT 15

( 2 ) INFORMATION FOR SEQ ID NO:15:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( i i ) MOLECULE TYPE: synthetic DNA ( i x ) FEATURE:
      ( A ) NAME/KEY: 3'biotin
      ( B ) LOCATION: 15

( x i ) SEQUENCE DESCRIPTION: SEQ ID NO:15:

CTTGCTCATT GACCT 15

( 2 ) INFORMATION FOR SEQ ID NO:16:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( i i ) MOLECULE TYPE: synthetic DNA ( i x ) FEATURE:
      ( A ) NAME/KEY: 3'biotin
      ( B ) LOCATION: 15

( x i ) SEQUENCE DESCRIPTION: SEQ ID NO:16:

GCTCATTGAT CTCCA 15

( 2 ) INFORMATION FOR SEQ ID NO:17:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( i i ) MOLECULE TYPE: synthetic DNA ( i x ) FEATURE:
      ( A ) NAME/KEY: 3'biotin
      ( B ) LOCATION: 15

( x i ) SEQUENCE DESCRIPTION: SEQ ID NO:17:

GCTCGTTGAT CTCCA 15

( 2 ) INFORMATION FOR SEQ ID NO:18:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( i i ) MOLECULE TYPE: synthetic DNA ( i x ) FEATURE:
      ( A ) NAME/KEY: 3'biotin
      ( B ) LOCATION: 15

( x i ) SEQUENCE DESCRIPTION: SEQ ID NO:18:

GCTCATTGAC CTCCA 15

( 2 ) INFORMATION FOR SEQ ID NO:19:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: synthetic DNA ( i x ) FEATURE:
        ( A ) NAME/KEY: 5'biotin
        ( B ) LOCATION: 1

( i x ) FEATURE:
        ( A ) NAME/KEY: 3'fluorescein hapten
        ( B ) LOCATION: 24

( x i ) SEQUENCE DESCRIPTION: SEQ ID NO:19:

GGACACGGAC ACGGACACGG ACAC 24

( 2 ) INFORMATION FOR SEQ ID NO:20:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: synthetic DNA ( i x ) FEATURE:
        ( A ) NAME/KEY: 5'biotin
        ( B ) LOCATION: 1

( i x ) FEATURE:
        ( A ) NAME/KEY: 3'quinoline hapten
        ( B ) LOCATION: 24

( x i ) SEQUENCE DESCRIPTION: SEQ ID NO:20:

GGACACGGAC ACGGACACGG ACAC 24

( 2 ) INFORMATION FOR SEQ ID NO:21:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: synthetic DNA ( i x ) FEATURE:
        ( A ) NAME/KEY: 5'biotin
        ( B ) LOCATION: 1

( i x ) FEATURE:
        ( A ) NAME/KEY: 3'adamantane hapten
        ( B ) LOCATION: 24

( x i ) SEQUENCE DESCRIPTION: SEQ ID NO:21:

GGACACGGAC ACGGACACGG ACAC 24

LIGHT SCATTERING OPTICAL WAVEGUIDE METHOD FOR DETECTING SPECIFIC BINDING EVENTS

This is a division of U.S. patent application Ser. No. 08/311,462 filed Sep. 22, 1994 now U.S. Pat. No. 5,599,668

FIELD OF THE INVENTION

The invention relates to several fields, especially specific binding partner interactions, evanescent waveguides and light scattering. More particularly, the invention relates to a process of detecting one or more specific binding analytes, especially DNA or oligonucleotides, through light scattering techniques, the scattering being caused by a particulate label held by specific binding forces within the penetration depth of the evanescent wave of a waveguide.

BACKGROUND OF THE INVENTION

Total internal reflection ("TIR") is known in the art and is described with reference to FIG. 1. TIR operates upon the principle that light 10 traveling in a denser medium 12 (i.e. having the higher refractive index, $N_1$) and striking the interface 14 between the denser medium and a rarer medium 16 (i.e. having the lower refractive index, $N_2$) is totally reflected within the denser medium 12 if it strikes the interface at an angle, $\theta_R$, greater than the critical angle, $\theta_C$, where the critical angle is defined by the equation:

$$\theta_C = \arcsin (N_2/N_1)$$

Under these conditions, an electromagnetic waveform known as an "evanescent wave" is generated. As shown in FIG. 1B, the electric field associated with the light in the denser medium forms a standing sinusoidal wave 18 normal to the interface. The evanescent wave penetrates into the rarer medium 16, but its energy E dissipates exponentially as a function of distance Z from the interface as shown at 20. A parameter known as "penetration depth" ($d_p$—shown in FIG. 1A at 22) is defined as the distance from the interface at which the evanescent wave energy has fallen to 0.368 times the energy value at the interface. [See, Sutherland et al., *J. Immunol. Meth.*, 74:253–265 (1984) defining $d_p$ as the depth where $E=(e^{-1}) \cdot E_0$. Penetration depth is calculated as follows:

$$d_p = \frac{\lambda/N_1}{2\pi \{\sin^2\theta_R - (N_2/N_1)^2\}^{1/2}}$$

Factors that tend to increase the penetration depth are: increasing angle of incidence, $\theta_R$; closely matching indices of refraction of the two media i.e. $N_2/N_1 \rightarrow 1$); and increasing wavelength, $\gamma$. For example, if a quartz TIR element ($N_1$= 1.46) is placed in an aqueous medium ($N_2$=1.34), the critical angle, $\theta_C$, is 66° (=arcsin 0.9178). If 500 nm light impacts the interface at $\theta_R$=70° (i.e. greater than the critical angle) the $d_p$ is approximately 270 nm.

Within the penetration depth, the evanescent wave in the rarer medium (typically a reaction solution) can excite fluorescence in the sample. This phenomenon has been used in the art with respect to immunoassays Harrick, et al. ,*Anal. Chem.* 45:687 (1973). Devices and methods that use TIR fluorescence for immunoassays have been described in the art by Hirschfield, U.S. Pat. Nos. 4,447,564, 4,577,109, and 4,654,532; Hirschfield and Block, U.S. Pat. Nos. 4,716,121 and 4,582,809, and U.S. Ser. No. 07/863,553 published as WO 93/20240 (Abbott Labs), which are all incorporated herein by reference. An immunospecific agent is adhered to the surface of the element and allowed to react with fluorescently labeled specific binding partners in the rarer medium. The specific binding results in the fluorescent labels being bound within the penetration depth. The emitted fluorescence (at the shifted wavelength) tunnels back into the TIR element, propagates within the TIR element along the same path as the standing sinusoidal wave (but at a different wavelength) and is detected at the output of the element.

TIR has also been used in conjunction with light scattering detection in a technique referred to as Scattered Total Internal Reflectance ("STIR"). See, e.g., U.S. Pat. Nos. 4,979,821 and 5,017,009 to Schutt, et al and WO 94/00763 (Akzo N.V.). According to this technique, a beam of light is scanned across the surface of a TIR element at a suitable angle and the light energy is totally reflected except for the evanescent wave. Particles such as red blood cells, colloidal gold or latex specifically bound within the penetration depth will scatter the light and the scattered light is detected by a photodetection means. WO 94/00763 also describes scanning the light beam across several loci of specific binding members which are either (1) the same binding member at varying concentration to achieve a wider dynamic range, or (2) different binding members to test for different analytes in a multiplex format. Scanning the light beam across multiple sites and gathering scattered light at each one is a very time-consuming process.

In U.S. Pat. No. 4,608,344 to Carter, et al., an optical waveguide is employed as the TIR element. In one variation, multiple binding sites are arranged on the waveguide in specific lines or grids to create a diffraction grating pattern of scattered light. By then looking at only specific orders of scattered light, this techniques minimizes the scattering caused by surface imperfections and/or impurities such as dust particles. (see FIG. 14 and columns 17–19).

Practical use of the Carter and STIR devices is severely limited by the serious background scattering from particles in solution. This background limits the sensitivity of detection of bound particles associated with analyte. The poor performance was compensated by sophisticated electronics and optics that could discriminate the small amount of signal over the high background levels. Electronic and optic complexity result in very expensive systems.

Finally, U.S. Pat. No. 5,192,502 to Attridge, et al., teaches a device comprising parallel plates defining a cavity for receiving a sample fluid. One plate serves as a waveguide and the other is coated with a layer of a light absorbing material.

Other background art of interest include the disclosure of Drmanac, et al. U.S. Pat. No. 5,202,231 which describes a new technique for the generation of nucleic acid sequence information known as sequencing by hybridization (SBH). According to this technique, a solid phase containing bound thereto an array of oligonucleotides of known sequence is allowed to hybridize with labeled DNA from a sample. Thus, a single hybridization experiment allows examination of a large number of different sites on a DNA molecule. Diagnosis of several human genetic conditions such as Duchenne muscular dystrophy or cystic fibrosis will likely require the resolving power of an SBH type system to determine the mutation associated with the disease state in an accurate and cost effective manner. One particular implementation of the SBH method uses a large number of oligonucleotides immobilized in a high density two dimensional array. Such a device has been called a "DNA chip" analogous to the high density circuits produced by the electronics industry. A sample of unknown DNA is applied to the chip and the pattern of hybridization determined and analyzed to obtain sequence information. WO 92/10588 and WO 92/10092 (Affymax Technologies N.V.) contain similar disclosures, as well as a photolithographic method for manufacturing such chips.

Since the stringency conditions affect hybridization, fine differentiation and specificity can be obtained if stringency can be accurately controlled. Thus, melting curves could provide an additional dimension to the DNA chip system and allow better differentiation of closely related sequences, a concern in implementation of SBH technology. The ability to change temperature and, in real time, monitor the chip hybridization patterns would be of great utility, particularly where there is a wide variation in GC content. Livshits, et al. *I. Biomol. Struct. & Dynamics*, 11:783–795 (1994) describe a DNA sequencing technique where discrimination of perfect and imperfect hybridizations was possible in a system of gel immobilized DNA using radioactive or fluorescent labels. The gel was subjected to one-minute washes every 5° C. to remove label associated with imperfectly hybridized DNA. The authors claim the gel was advantageous due to a higher capacity for immobilization and higher discrimination power than other surfaces. However, the need to wash excess label from the surface, as well as the relatively long time for scanning the entire surface to obtain a measurement, impose significant limitations. For example, if one minute is required to read an entire DNA chip array and a one minute wash is needed at each incremental temperature, then a high resolution melting curve (e.g. every 1° C.) from 30° to 70° C. would require an hour. The temperature would have to be held constant for one minute at each incremental temperature until all spots on the chip are measured.

Also of interest is the disclosure of co-owned, co-pending U.S. application Ser. No. 08/140,383, filed Oct. 21, 1993 and entitled APPARATUS AND METHOD FOR DETECTING A TARGET LIGAND, incorporated herein by reference. This application describes the use of a charge-coupled device "CCD" camera and image handling software to image and detect specific binding target ligands arranged in spatially separated, multiple loci on a single solid phase.

SUMMARY OF THE INVENTION

One challenge faced by the Human Genome Project in completely sequencing the human genome is to increase the rate of acquisition of DNA sequence data by two orders of magnitude. The present application describes, as a preferred embodiment, a detection method using a two dimensional optical waveguide which allows measurement of real time binding or melting of a light scattering label at multiple capture sites on a support comprising a DNA array. This permits collection of hybridization data as rapidly as video recording permits. The methods rely on scattering of the evanescent wave, whereby only label confined within the penetration depth generates signal. Imaging of the scattered light permits interrogation of the entire array simultaneously. Hybridization specificity is equivalent to that obtained with a conventional system and autoradiography. Melting curves are consistent with liquid phase melting curves for the same sequence combinations, and differences of as little as a single base pair are easily distinguishable. Limiting dilution established detection of targets at concentrations as low as about 0.4 nM, which is comparable to the best current fluorescence based systems. It is anticipated that this methodology will provide a powerful tool for rapid, cost effective, detection of sequence variations.

Thus, in one aspect, the present invention is a method for detecting the presence or amount of one or more specific binding analytes in a fluid sample, the method comprising:

(a) providing a waveguide device, the waveguide device comprising (i) a transparent element having a refractive index greater than that of the fluid sample; (ii) a light receiving edge; and (iii) a reactive surface comprising a first specific binding member of at least one cognate binding pair immobilized at a plurality of sites on the surface of the element, other non-situs portions of the reactive surface having no specific binding member immobilized thereon; wherein said first specific binding member, through intermediate cognate binding pairs if desired, is capable of specifically binding at least one analyte;

(b) contacting the reactive surface with a sample suspected to contain said one or more analytes and with a light scattering label attached to a specific binding member of a second cognate binding pair which, through intermediate cognate binding pairs if desired, is capable of specifically binding said one or more analytes, in the case of a sandwich assay, or the immobilized first specific binding member of said first cognate binding pair, in the case of a competitive assay; thereby forming light scattering label complexes attached to the plurality of sites in proportion to the amount of analyte in the sample;

(c) illuminating the light receiving edge of the waveguide with light effective to create total internal reflection within the waveguide, thereby simultaneously illuminating the entire reactive surface;

(d) substantially simultaneously collecting scattered light, if any, from each situs and from non-situs portions of said surface;

(e) comparing the degree of light scattering at each situs with either (i) the degree of light scattering at a non-situs portion, or (ii) the degree of light scattering at another situs, or both, whereby light scattering at each situs correlates to the presence or amount of the analyte for which the immobilized specific binding member at that situs is specific.

According to the above method, there are multiple sites on a single waveguide; the waveguide is illuminated all at once and scattering from all sites is instantaneously collected, either by photodetectors or visually.

In a separate aspect, the invention is a method for visually detecting the presence or approximate amount of at least one specific binding analyte in a fluid sample, the method comprising:

(a) providing a waveguide device, the waveguide device comprising (i) a transparent element having a refractive index greater than that of the fluid sample; (ii) a light receiving edge; and (iii) a reactive surface comprising a first specific binding member of at least one cognate binding pair immobilized on at least one test situs on the surface of the element, other non-situs portions of the reactive surface having no specific binding member immobilized thereon; wherein said first specific binding member, through intermediate cognate binding pairs if desired, is capable of specifically binding said analyte;

(b) contacting the reactive surface with the sample suspected to contain said analyte and with a light scattering label attached to a first specific binding member of a second cognate binding pair which, through intermediate cognate binding pairs if desired, is capable of specifically binding said analyte, in the case of a sandwich assay, or the immobilized first specific binding member, in the case of a competitive assay; thereby forming light scattering label complexes attached to the situs in proportion to the amount of the analyte in the sample;

(c) illuminating the light receiving edge of the waveguide with light effective to create total internal reflection within the waveguide;

(d) visually examining the reactive surface for light scattering and comparing the degree of light scattering at the test situs with either (i) the degree of light scattering at a non-situs portion, or (ii) the degree of light scattering at another situs, or both, whereby scattering at the situs correlates to the presence or amount of said analyte.

This method is not limited to multiple sites, but does require visual detection.

Another aspect, also not limited to multiple sites, is a determination of scattering using a rate-read technique. Thus, in this aspect the invention comprises:

(a) providing a waveguide device, the waveguide device comprising (i) a transparent element having a refractive index greater than that of the fluid sample; (ii) a light receiving edge; and (iii) a reactive surface comprising a first specific binding member of at least one cognate binding pair immobilized at a situs on the surface of the element, other non-situs portions of the reactive surface having no specific binding member immobilized thereon; wherein said first specific binding member, through intermediate cognate binding pairs if desired, is capable of specifically binding said analyte;

(b) contacting the reactive surface with the sample suspected to contain said analyte and with a light scattering label attached to a first specific binding member of a second cognate binding pair which, through intermediate cognate binding pairs if desired, is capable of specifically binding said analyte, in the case of a sandwich assay, or the immobilized first specific binding member, in the case of a competitive assay; thereby forming light scattering label complexes attached to said situs in proportion to the amount of analyte in the sample;

(c) illuminating the light receiving edge of the waveguide with light effective to create total internal reflection within the waveguide, thereby simultaneously illuminating the entire reactive surface;

(d) substantially simultaneously collecting scattered light, if any, from said situs and from non-situs portions of said surface at a first time, $t_1$, using a photodetector device;

(e) repeating steps (c) and (d) at least once to collect scattered light, if any, from said situs and non-situs portions at a second time, $t_2$; and (f) comparing the degree of light scattering at said situs at time $t_1$ with the degree of light scattering at said situs at time $t_2$, whereby the light scattering at the situs correlates to the presence or amount of the specific analyte, and the difference over time in scattering of light provides kinetic information indicative of the amount of analyte present at said situs.

This aspect can be applied to single or multiple sites, but it is unlikely that visual detection is possible since subtle variations in signal can appear over time. Timed readings can be made continuously or discretely. In continuous reading, initial rates can be determined from the initial slope of the time course.

A particularly useful application for the invention is in real-time oligonucleotide melting studies. Accordingly, in another aspect the invention relates to a method for determining the nucleotide sequence of segment of unknown nucleic acid or for distinguishing two closely related nucleotide sequences, the method comprising:

(a) providing a waveguide device, the waveguide device comprising (i) a transparent element having a refractive index greater than that of the fluid sample; (ii) a light receiving edge; and (iii) a reactive surface comprising a plurality of sites having oligonucleotide immobilized thereon, said sites defining an array of oligonucleotides having different sequences for hybridizing with the unknown nucleic acid, other non-situs portions of the surface of said element having no oligonucleotides immobilized thereon;

(b) contacting the reactive surface under hybridizing conditions with said unknown nucleic acid wherein said unknown nucleic acid, either directly or through intermediate cognate binding pairs if desired, is labeled with a light scattering label; thereby forming light scattering label complexes attached to those sites of the reactive surface which are complementary to the sequence of the unknown nucleic acid;

(c) illuminating the light receiving edge of the waveguide with light effective to create total internal reflection within the waveguide, thereby simultaneously illuminating the entire reactive surface;

(d) substantially simultaneously collecting scattered light, if any, from each situs and from non-situs portions of said surface;

(e) comparing the degree of light scattering at each situs with either (i) the degree of light scattering at a non-situs portion; or (ii) the degree of light scattering at another situs; and (f) further comprising incrementally increasing the stringency conditions at the reactive surface of the waveguide device to initiate dissociation of bound nucleic acid from the sites and repeating steps (d) and (e) at each increment;

whereby single base pair differences between the oligonucleotides and the unknown nucleic acid can be distinguished from perfect matches by differences in dissociation properties.

Finally, in an aspect not restricted to two-dimensional waveguides or even to simultaneous illumination, the invention also relates to an improved method for light scattering which give reduced backgrounds. Thus, the invention is also a method for detecting the presence or amount of a specific binding analyte in a fluid sample, the method comprising:

(a) providing a TIR device, the device comprising (i) a transparent TIR element having a refractive index greater than that of the fluid sample; (ii) a light receiving edge; and (iii) a reactive surface comprising a first specific binding member of at least one cognate binding pair immobilized on at least one situs on the surface of the element, other non-situs portions of the reactive surface having no specific binding member immobilized thereon; wherein said first specific binding member, through intermediate cognate binding pairs if desired, is capable of specifically binding said analyte;

(b) contacting the reactive surface with (i) the sample suspected to contain said analyte; (ii) a light scattering label attached to a first specific binding member of a second cognate binding pair which, through intermediate cognate binding pairs if desired, is capable of specifically binding said analyte, in the case of a sandwich assay, or the immobilized first specific binding member, in the case of a competitive assay, thereby forming light scattering label complexes attached to said situs in proportion to the amount of analyte in the sample; and (iii) a solution of a light absorbing member sufficient to impart an effective O.D. of at least 15;

(c) illuminating the light receiving edge of the TIR element with light effective to create total internal reflection within the element;

(d) detecting the scattered light and comparing the degree of light scattering at the situs with the degree of light scattering at a non-situs portion, whereby background scattering is minimized by absorbance by the light absorbing material.

In all of the above aspects, the specific binding analyte may be an oligonucleotide or nucleic acid. It may also be an antigen or antibody in most aspects. While all aspects preferably have multiple sites, certain aspects do not require this. The number of "multiple" or "plurality" of sites may be as few as two or as many as several thousand.

In each of the above aspects, the waveguide element may comprise a planar surface, such as a glass plate. In each aspect, it is possible to provide a second plate which is fastened to the element to form a capillary channel therebetween. The reaction surface should face into the channel so that the channel can be used as a reaction vessel to flow reagents over the reactive surface. Also, it is preferred in each aspect, to coat the surface with a metasoluble protein such as casein. This coating serves to block non-specific binding sites and to facilitate the flow of liquids over the surface.

The light scattering label (LSL) in all cases can be colloidal particles, such as colloidal gold or selenium or minute latex particles. It is also possible in all embodiments to utilize a liquid absorbing member (LAM) in the solution on the reaction surface. This has the advantage of reducing background scattering very near to its source. The LAM increased the O.D. of the solution to at least 15 and provides a dark background against which scattering at the sites shows as a bright area.

BRIEF DESCRIPTION OF THE DRAWINGS

FIG. 1 shows the reflection of light at an interface and, on the right, a plot of the electric field energy E as a function of the distance Z from the interface.

FIG. 2C is an enlarged cross section taken along line C—C of FIG. 2B.

DETAILED DESCRIPTION OF THE INVENTION

The various aspects of the present invention will now be described in more detail.

TIR Elements and Waveguide Devices

The physical principles of total internal reflection ("TIR") and evanescent waves are set forth in the background section. As used herein, "TIR element" refers to any transparent material that provides an interface capable of total internal reflection. The element may be, for example, a cuvette, a rod or a plate. The evanescent wave of a TIR element may exist only at the point or points of total internal reflection. In contrast, a "waveguide" refers to a two dimensional TIR element such that light is totally internally reflected at multiple points, thereby creating an evanescent wave that is substantially uniform across all or nearly all of the surface. A two dimensional waveguide may be planar or curvelinear in configuration. For simplicity, a planar waveguide is described as the preferred embodiment.

Figure 2A:
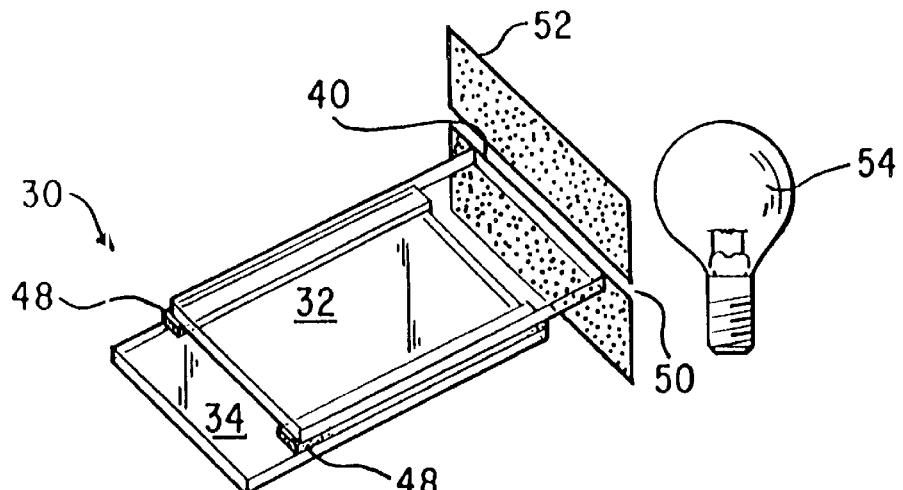
FIGS. 2A, 2B and 2C are, respectively, perspective, side and cross section views of a device according to an embodiment of the invention.
Figure 2B:
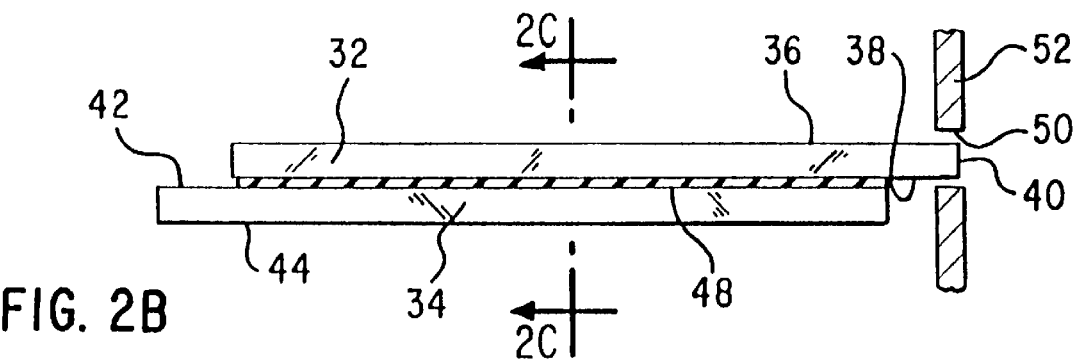
Figure 2C:
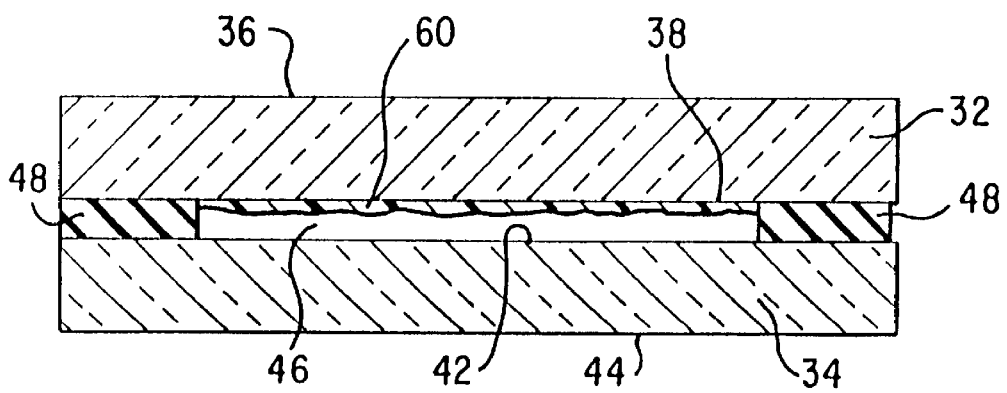
Figure 4:
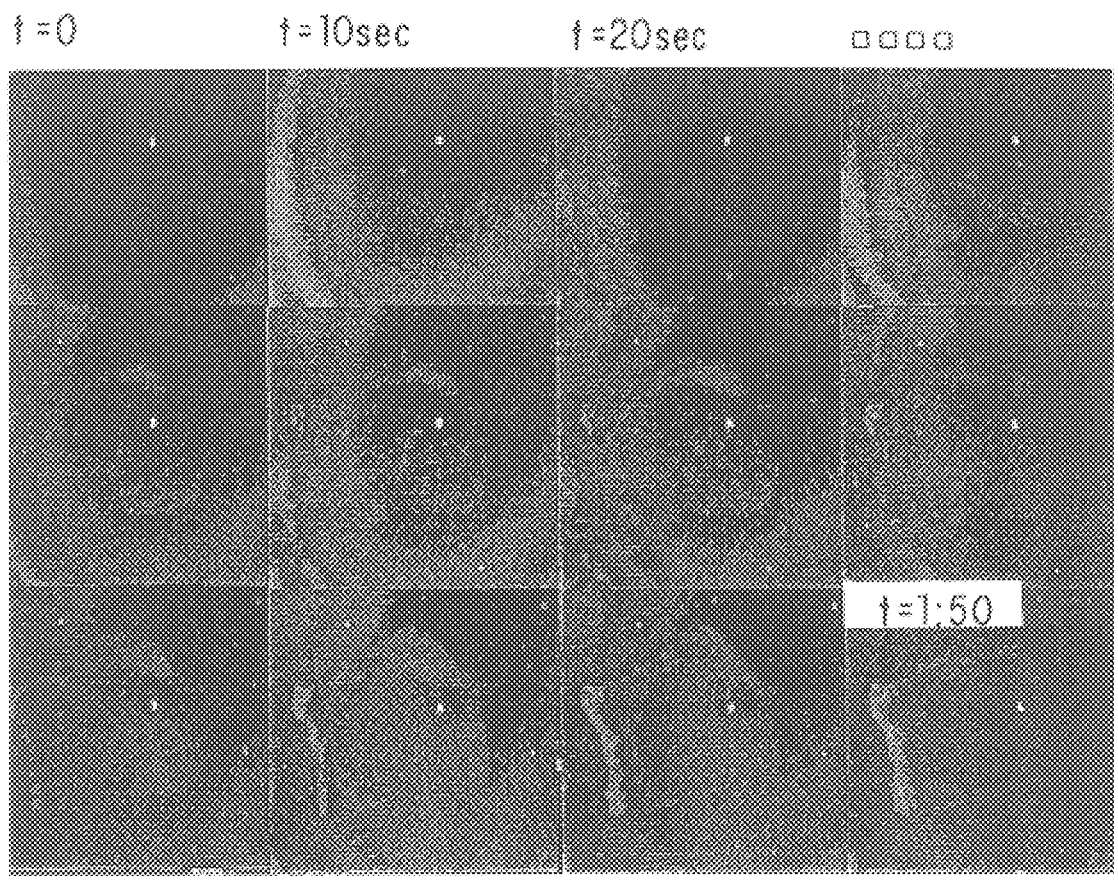
FIGS. 4,5,6,7,8A, and 9,10,11 (1–6) and 12(a–e) are printed representations of the actual video images taken of the waveguides as described in more detail in the examples. The video images were fed to an 8-bit frame grabber which digitized the information. The digitized file was imported into a drawing application from which it was printed on a high resolution printer.
Figure 5A:
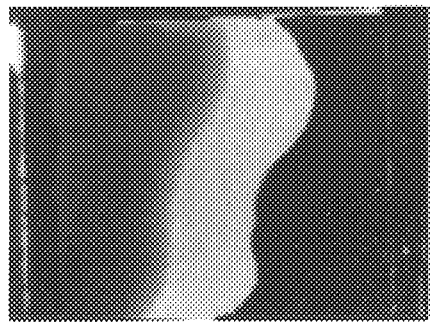
Figure 5B:
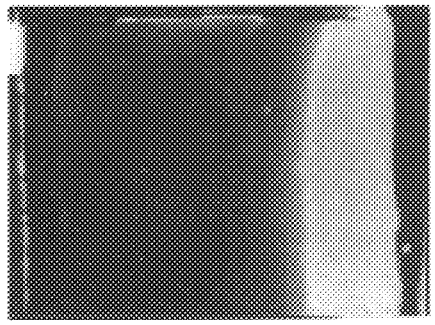
Figure 5C:
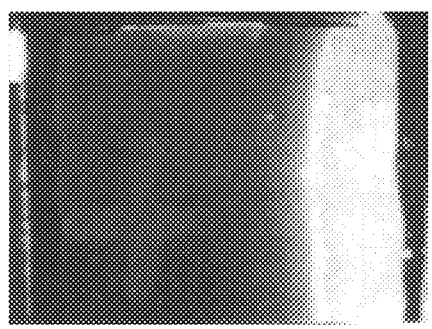
Figure 5D:
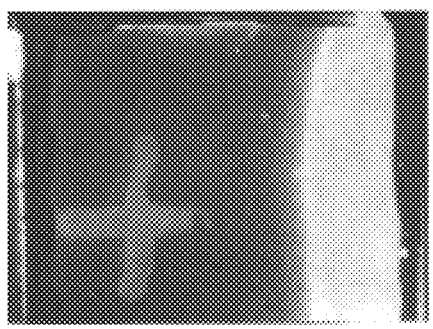
Figure 6A:
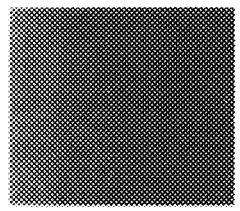
Figure 6B:
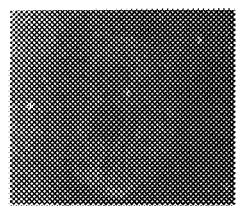
Figure 6C:
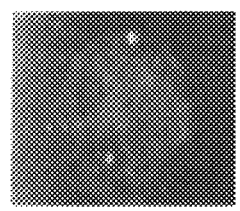
Figure 6D:
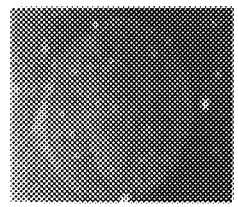
Figure 6E:
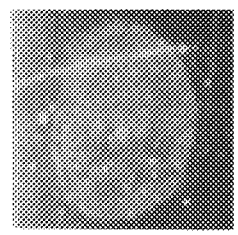
Figure 6F:
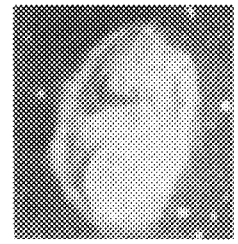
Figure 7A:
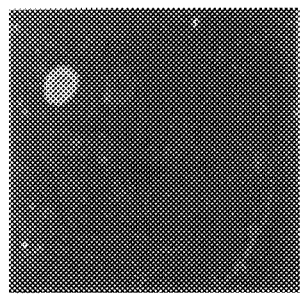
Figure 7B:
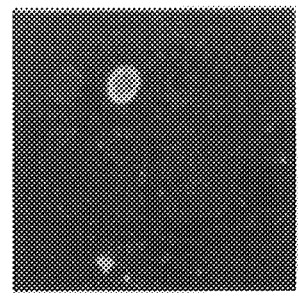
Figure 7C:
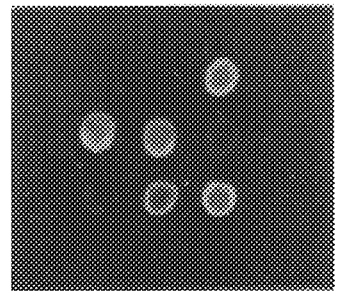
Figure 7D:
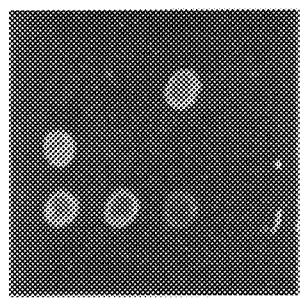
Figure 7E:
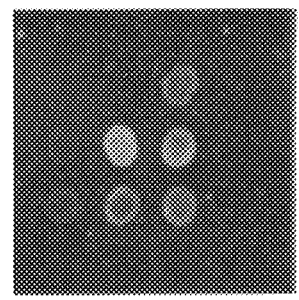
Figure 7F:
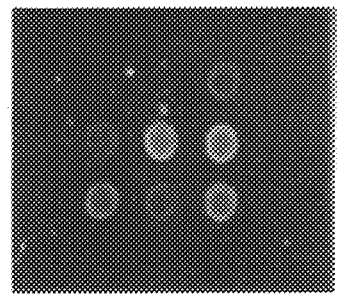
Figure 7G:
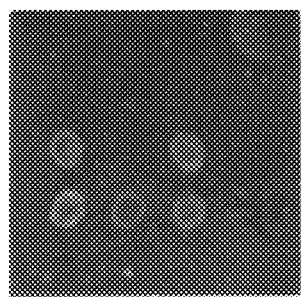
Figure 7H:
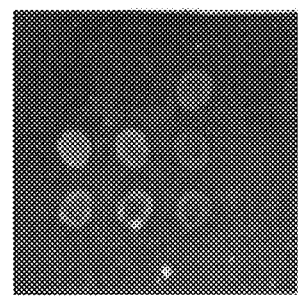
Figure 7I:
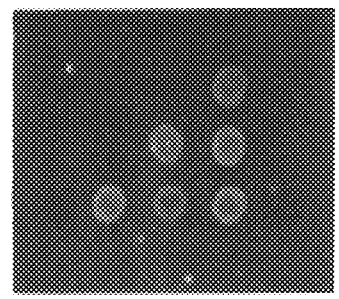

In one preferred embodiment of the present invention the TIR element is a two dimensional waveguide. FIGS. 2A–2C illustrate a preferred embodiment, wherein a waveguide device 30 comprises a planar waveguide element 32 and a parallel planar plate 34. The waveguide element thus has parallel surfaces 36 and 38 as well as a light-receiving edge 40. Similarly, the plate 34 has parallel surfaces 42 and 44. The waveguide element 32 and the plate 34 are held together in spaced parallel fashion, such that the element surfaces 38 and the plate surface 42 define a narrow channel 46. The element and plate may be held together by any convenient means, including adhesive means 48 consisting of double stick tape disposed along the edges of the element and plate. The channel 46 is preferably rather small so as to enable capillary transfer of a fluid sample therethrough. For example, the height should be less than about 1mm, preferably less than about 0.1 mm.

The element 32 should be made of an optically transparent material such as glass, quartz, plastics such as polycarbonate, acrylic, or polystyrene. The refractive index of the waveguide must be greater than the refractive index of the sample fluid, as is known in the art for effecting total internal reflectance. For an aqueous sample solution, the refractive index, n, is about 1.33, so the waveguide typically has a refractive index of greater than 1.35, usually about 1.5 or more. The waveguide may be a piece of plastic or glass, for example, a standard glass microscope slide or cover slip may be used.

The plate 34 may be constructed of similar materials. As seen in FIGS. 2A and 2B, the light receiving end 40 of the waveguide element 32 is disposed in a narrow slit 50 of a mask 52 in order to minimize the effects of stray light originating from the light source 54. Minimization of stray light is also improved by the use of light absorbing materials as discussed below.

Light source 54 for generating the incident light beam may be nearly any source of electromagnetic energy, including energy in the visible, ultra-violet, and near-IR spectra. The term "light" is thus construed quite broadly and is not confined to the visible range, except in the embodiments that are visually detected. Non-visible wavelengths are detected by detectors optimized for the particular wavelength as is well known in the art. The light may be monochromatic or polychromatic, collimated or uncollimated, polarized or unpolarized. Preferred light sources include lasers, light emitting diodes, flash lamps, arc lamps, incandescent lamps and fluorescent discharge lamps. The light source used to illuminate the waveguide element can be a low wattage helium-neon laser. For a portable disposable such as that described in example 1 below, the light source can be a small incandescent light bulb powered by a battery, such as is used in pocket flashlight. Preferably, the light source includes potentiometer means for varying the intensity of the light source. Alternatively, filters and/or lenses may be employed to adjust the intensity to a suitable level.

Detection means for determining the degree of light scattering are described in detail below but briefly comprise both instrument and visual means. It is an important feature of the invention that light scattering events across the entire waveguide can be monitored essentially simultaneously, whether by the eye and brain of an observer or by photo-detection devices including CCD cameras forming images that are digitized and processed using computers. In each case only a single, multi-functional reactive surface is used and is illuminated simultaneously by the evanescent wave.

Reactive Surfaces

According to the invention, a reactive surface consisting of at least one situs is formed on one side of the waveguide element. While some embodiments may have only a single test situs, the invention best utilizes a plurality of such sites, and multiple-situs devices will be described herein. Multiple test sites may contain the same or different specific binding members. A "situs" (plural="sites" herein) is defined as the delimited area in which a specific binding member for an analyte is immobilized, it being understood that non-situs portions of the surface will also exist outside of the delimited area. The immobilized specific binding member is referred to herein as a "capture member" or "capture SBM". Preferably the situs is a small spot or dot and the non-situs portions surround the situs. Of course many other situs sizes and configurations are possible and within the invention. A situs may also be configured as a line or bar; as a letter or numeral; as a circle, rectangle or triangle; or as any other graphic such as, for example, any graphic typically employed in computer icon or clip-art collections.

The area (size) of a situs need be large enough only to immobilize sufficient specific binding member to enable capture of the labeled analyte and light scattering particle. This is dependent in part on the density of the situs, as discussed below. For example, situs areas of as little as 150 μm diameter have been used successfully (see example 7 and FIG. 10). Such small areas are preferred when many sites will be placed on a reactive surface, giving a high "site density". The practical lower limit of size is about 1 μm in diameter. For visual detection, areas large enough to be detected without magnification are desired; for example at least about 1 to about 50 mm$^2$; up to as large as 1 cm$^2$ or even larger. There is no upper size limit except as dictated by manufacturing costs and user convenience; any desired situs size or shape is suitable.

Multiple situs devices may contain the same or different SBMs at each situs. If the same, the plurality of sites may have similar concentrations and thereby offer replicate information or may have varying concentrations of the SBM, thereby offering semi-quantitation or calibration against a standard. If the SBMs are different, the device may be utilized for multiplex detections of several analytes simultaneously. In one special case of different SBMs, one or more situs can serve as a positive control. Of course, combinations of all the above (e.g. multiplexed semiquantitative determinations) are possible in devices with many sites.

For multiple situs devices, the sites may be arranged in any convenient pattern or array. The spacing between sites will depend on the resolution of the detection system, described below, and the manufacturing process used to create the situs. Subject to manufacturing capability, the higher the resolution of detection, the closer the sites may be. There should be sufficient separation of the immobilized capture SBMs that the reaction of each of these members individually with the corresponding binding member in a fluid sample and/or a light-scattering labeled member can be differentiated from a reaction at another site without substantial interference due to nearby immobilized binding pair members and their associated light scattering particles. Preferably a non-situs portion clearly separates each and every situs. A very simple array is a Cartesian grid but multiple sites may be configured as lines, patterns and other graphics as well. In multiple-situs reaction surfaces one or more sites will often represent a positive control, a negative control, a series of calibration standards or a combination of any of these.

One preferred situs configuration is the shape of a cross, which results in a "plus" symbol in the event of a positive result. In a variation of this, only the vertical portion or portions of the cross are analyte binding situs, while the horizontal aspect of the plus contains a binder specific for label which is independent of the presence of analyte. Such a configuration is described in U.S. Pat. No. 5,008,080, "Solid Phase Analytical Device and Method for Using Same", to Brown et al. Configurations of this variation operate as a verification of the assay by producing a minus "−" symbol whether analyte is present or not, and producing a plus "+" symbol when analyte is present. Besides the "plus/minus" verification configuration, other shapes of this variation are also possible, as disclosed in the cited patent.

In the two-plane device of FIGS. 2A–2C, the reactive surface 60 is preferably formed on the surface 38 of waveguide element 34 which faces into the channel 48. See FIG. 2C. This facilitates the contacting of sample and/or light-scattering label reagent with the situs of the reactive surface by permitting capillary flow across the reactive surface. Flow can be enhanced by the use of an absorbent or bibulous material such as paper at one end of the channel. Of course, the two-plane device is but one embodiment. A single two dimensional waveguide element can also be used, the reaction surface being coated on one side. It may need to be oriented with the reaction surface in an upwardly facing direction, however, to facilitate contact with the sample and light scattering label reagent. Scattering of light in the evanescent wave may then be observed from the underside, using a mirror if desired.

Specific Binding Members and Immobilization on the Reactive Surface

In the process of the invention, one or more capture members are first immobilized onto the surface of an optical waveguide to form a reactive surface. A specific binding member ("SBM") is either member of a cognate binding pair. A "cognate binding pair" is any ligand-receptor combination that will specifically bind to one another, generally through non-covalent interactions such as ionic attractions, hydrogen bonding, Vanderwaals forces, hydrophobic interactions and the like. Exemplary cognate pairs and interactions are well known in the art and include, by way of example and not limitation: immunological interactions between an antibody or Fab fragment and its antigen, hapten or epitope; biochemical interactions between a protein (e.g. hormone or enzyme) and its receptor (for example, avidin or streptavidin and biotin), or between a carbohydrate and a lectin; chemical interactions, such as between a metal and a chelating agent; and nucleic acid base pairing between complementary nucleic acid strands. A recently reported specific binding member is the peptide nucleic acid analog, or "PNA", described in WO 92/20702 and WO 92/20703, both to Buchardt, et al., and in Flam, *Science*, 262: 1647, (1993), which forms a cognate binding pair with nucleic acids or other PNAs. Nucleic acid will be understood to include 2'-deoxyribonucleic acid (DNA) as well as ribonucleic acid (RNA) when stability permits.

Preparation of antibody SBMs is an old and well known technique and need not be described in detail. Briefly, an animal is immunized or challenged with the desired hapten according to an immunization schedule. Often the hapten is coupled to a carrier molecule such as BSA to improve recognition. After a suitable time period, the animal is bled and antibodies are extracted. Alternatively, antibody can be obtained from ascites fluid. Highly specific monoclonal antibodies can be prepared if desired using the now conventional techniques of Kohler and Milstein, *Nature*, 256, 495 (1975). Antibodies have numerous amino, carboxyl and sulfhydryl groups that might be utilized for coupling reactions.

Synthesis of oligonucleotide SBMs is also fairly routine, using automated synthesizers such as the ABI 480. These instruments prepare oligonucleotides of virtually any desired sequence in lengths up to about 75–100 bases. Longer polynucleotides, if desired, can be prepared by known cloning techniques or by synthesis of shorter segments and assembly. If desired, oligonucleotides can be modified with terminal amines or other reactive groups for coupling. A somewhat dated but still useful review of coupling chemistries is found in Goodchild, *Bioconjugate Chemistry*, 1(3):165–187 (1990).

SBMs may be covalently attached to the waveguide through chemical coupling means known in the art. The reactive surface may be derivatized directly with a variety of chemically reactive groups which then, under certain conditions, form stable covalent bonds with the applied SBM. Alternatively, the reactive surface may first be coated with chemically-derivatized polymers, such as dextran or PEG, which then form covalent bonds with applied SBMs. Certain types of detergents may also be coated to the reactive surface, then derivatized, in situ, and reacted with SBMs. For example, glass and quartz waveguides contain groups that can be activated to reactive hydroxyl and siloxy groups, which can be coupled to specific binding members via linkers. Such linkers include, for example, known homo- and hetero-bifunctional linkers.

It is, of course, preferable to link SBMs to the reactive surface in such a manner that the specific binding properties of the binding member are not lost. For example, antibodies can be coupled via their Fc portion as taught in U.S. Pat. No. 5,191,066 (Bieniarz, et al); and oligonucleotides can be coupled via terminal amines or other functional groups. Linker arms as taught by U.S. Pat. No. 4,948,882 to Ruth, can be placed on "sterically tolerant" positions of base moieties to facilitate coupling to solid phases without loss of hybridization capabilities. In yet another method, the reactive surface may be coated with streptavidin through physical adsorption, then reacted with a biotin-labeled binding pair member to create a well characterized, biologically reactive surface.

More recently, WO 92/10092 (Affymax Technologies, N.V.; Fodor, et al.) described a method of synthesis of oligonucleotides directly on a solid support using photolithography techniques.

To the surprise of applicants, the capture SBM need not be covalently attached at the reactive surface. SBMs may be adsorbed or complexed on the surface using protein coating layers. The observation that the various noncovalent forces holding the capture SBM (e.g. DNA) and label SBM (e.g. antibody) in place are less labile than DNA hybridization forces was somewhat of a surprise. However, this is in part due to the fortuitous choice of conditions, namely ionic strength which allows for relatively low melting temperatures of DNA (see examples). It may be possible to increase the melting temperature (by increasing the ionic strength) to a point where the DNA duplex is no longer the weak link in the chain.

The density (quantity per unit area) of capture SBM on the reactive surface correlates positively with the sensitivity of the system. Using oligonucleotide SBMs, about 5000 DNA molecules per square $\mu$m can be achieved by the spotting methods described herein. Other methods of chip construction, for example the photolithography techniques mentioned above, may yield other densities. The estimated theoretical maximum density for nucleic acid SBMs is about 250,000 molecules per square $\mu$m. It is unlikely, however, that chips of this density can be attained or that they would provide optimal performance in view of the steric restrictions imposed. Optimal density for best sensitivity involves a trade off between maximizing the number of binding sites per unit area, and maximizing the access to such sites keeping in mind diffusion kinetics requirements and steric considerations.

Application of the capture SBM onto the reactive surface may be accomplished by any convenient means. For example, manual use of micropipets or microcapillary tubes may be conveniently used for spotting capture member onto the reactive surface. It is preferred, however, to use automate this process for convenience, reproducibility and cost-savings. Mechanized application is particularly desirable when the assay is used in large-scale testing, such as routine screening applications. Automated application methods include, for example, positive displacement pumps, X-Y positioning tables, and/or ink jet spraying or printing systems and the like.

When appropriate, the SBMs may first be put into a solution to facilitate the process of depositing the samples onto the reactive surface. Suitable solutions for this purpose have only the general requirement that, upon drying, the SBM substantially retains its specificity (i. e. its specific binding properties), and does not significantly interfere with the refractive properties of the element. The volume of solution to be deposited depends on the concentration of SBM in the solution. Ideally, solutions are prepared in a concentration range of about 0.5 to 500 $\mu$M, so that a small drop (ca. 2 $\mu$l) contains the desired amount of SBM. Typically, repeated applications of SBMs at lower concentrations are preferred so as not to waste SBM. These are repeated until sufficient SBM is present, taking care not to overlap the application at nearby sites. If desired, a crosslinking agent can be included to increase the amount of SBM at the capture site, provided the crosslinking agent does not interfere with the specific binding properties.

After the SBM has been deposited on one or more sites of the reactive surface, the member is allowed to dry and thereby become immobilized on the reactive surface. Evaporation is the preferred drying method, and may be performed at room temperature (about 25° C.). When desired, the evaporation may be performed at elevated temperature, so long as the temperature does not significantly inhibit the ability of the capture members to specifically interact with their corresponding binding pair members. For example, where the immobilized capture SBM is a protein, non-denaturing temperatures should be employed.

In addition to immobilization of capture SBM to the reactive surface, the reactive surface is preferably treated so as to block non-specific interactions between the reactive surface and analyte binding members in a fluid sample which is to be tested. In the case of a protein SBM (e.g. antigen, antibody or PNA) on the reactive surface, the blocking material should be applied after immobilization of the SBM. Suitable protein blocking materials are casein, zein and bovine serum albumin (BSA). Other blockers can be detergents and long-chain water soluble polymers. The blocking material may be conveniently applied to the reactive surface as an aqueous or buffered aqueous solution. The blocking solution may be applied to the reactive surface at any time after the first capture SBMs are immobilized. In the case of a nucleic acid SBM, the blocking material may be applied before or after immobilization of the SBM. Suitable blockers include those described above as well as 0.5% sodiumdodecyl sulfate (SDS) and 1× to 5× Denhardt's solution (1× Denhardt's is (0.02% Ficoll, 0.02% polyvinylpyrrolidone and 0.2 mg/ml BSA).

Casein has been found to be a preferred blocking material for both DNA and antibody SBMs and is available from Sigma Chemical, St Louis, Mo., (catalog no. C-3400). Casein belongs to a class of proteins known as "meta-soluble" proteins (see, e.g., U.S. Pat. No. 5,120,643 to Ching, et al, incorporated herein by reference) which require chemical treatment to render them more soluble. Such treatments include acid or alkaline treatment and are believed to perform cleavage and/or partial hydrolysis of the intact protein. Other meta-soluble proteins include zein (Sigma catalog no. Z-3625 and a non-albumin egg white protein (Sigma catalog no. A-5253). Casein is a milk protein having a molecular weight of about 23,600 (bovine beta-casein), but as used herein, "casein" or "alkaline treated" casein both refer to a partially hydrolyzed mixture that results from alkaline treatment as described in example 1 of U.S. Pat. No. 5,120,643. An electrophoresis gel (20% polyacrylamide TBE) of the so-treated casein shows a mixture of fragments predominantly having molecular weight less than 15,000, as shown by a diffused band below this marker.

It is possible that the blockers, particularly casein, impart a hydrophobic nature to the surface that facilitates the "sheeting" action described in the examples. "Sheeting" occurs when water applied to the surface can be tipped off the element in one cohesive drop rather than multiple small droplets. However, it is believed that the uniformity of the coating is more important than its hydrophobicity. Elements that are formed into channel devices as in example 1 preferably exhibit such sheeting action. This is thought to facilitate flow and diffusion within the channel.

It should be understood that the first specific binding member may be specific for the analyte through the intermediary of additional cognate pairs if desired. For example, an oligonucleotide SBM might be biotinylated and attached to the reactive surface via a biotin-avidin cognate binding pair. Such an attachment is described by Hansen in EP 0 139 489(Ortho). Similarly, an oligonucleotide might be attached to the reactive surface through a mediator probe as disclosed by Stabinsky in U.S. Pat. No. 4,751,177 (Amgen). When using intermediary cognate binding pairs, one must keep in mind that the total distance from the interface (at the reactive surface) to the light scattering label should not greatly exceed the penetration depth. In this regard, it has been estimated that the diameter of an immunoglobulin antibody is about 5 nm and that the length of DNA 20-mer (in β-helix form) is about 6.8 nm. This leaves room for multiple cognate pairs in a typical 200–300 nm penetration depth (see background). It also should be understood that the cognate binding interactions must withstand the subsequent reaction conditions which, for some applications, may include elevated temperatures. Longer oligonucleotides or ones with higher GC content are more stable and are preferred in this case.

Light Scattering Labels

Another important component of the present invention is the light-scattering label or particle ("LSL"). A LSL is a molecule or a material, often a particle, which causes incident light to be scattered elastically, i.e. substantially without absorbing the light energy. Exemplary LSLs include colloidal metal and non-metal labels such as colloidal gold or selenium; red blood cells; and dyed plastic particles made of latex, polystyrene, polymethylacrylate, polycarbonate or similar materials. The size of such particulate labels ranges from 10 nm to 10 $\mu$m, typically from 50 to 500 nm, and preferably from 70 to 200 nm. The larger the particle, the greater the light scattering effect, but this is true of both bound and bulk solution particles, so background also increases with particle size. Suitable particle LSLs are available from Bangs Laboratories, Inc., Carmel, Ind., USA.

In the present invention, the LSL is attached to first specific binding member of a second cognate binding pair. The second specific binding pair member may be referred to as a "label SBM" and the complex of LSL and label SBM is referred to as "label conjugate" or just "conjugate". The nature and specificity of the label SBM depends on the format of the assay. For a competitive assay format, the label SBM is an analog of the analyte and specifically binds with the capture SBM in competition with the analyte. For a direct sandwich assay format, the label SBM is specific for a second epitope on the analyte. This permits the analyte to be "sandwiched" between the capture SBM and the label SBM. In an indirect sandwich assay format, the label SBM is specific for a site or reporter group that is associated with the analyte. For example, once an antigenic analyte is captured, a biotinylated antibody may be used to "sandwich" the analyte, and biotin-specific label SBM is used. This indirect sandwich format is also useful for nucleic acids. In this case the capture SBM is an oligonucleotide complementary to the target and the target contains a specific binding reporter molecule (e.g. biotin or a hapten, typically incorporated via an amplification procedure such as LCR or PCR) and the label SBM is chosen to be specific for the reporter group.

Of course, the label SBM may be specific for its respective partner (analyte or first SBM, depending on the format) through intermediary cognate pairs, as was the case with the capture SBM. For example, if the analyte is an oligonucleotide such as an amplification product bearing a hapten reporter group, a sandwich assay format might include a LSL conjugated to antihapten antibody. Thus, the label SBM is specific for the analyte via the hapten-antihapten cognate binding pair. An example of a nucleic acid intermediary cognate pair is described in Schneider, et al., U.S. Pat. No. 4,882,269 (Princeton University). The same considerations of distance from the interface and stability of the cognate pairs should be considered for label SBMs as well as capture SBMs.

Regardless of the assay format the label SBM must be attached to the light scattering label to form the conjugate. As with capture SBMs, the label SBM may be covalently bonded to the LSL, but this is not essential. Physical adsorption of label SBM onto particulate LSLs is also suitable. In such case, the attachment need only be strong enough to withstand the subsequent reaction conditions without substantial loss of LSL, e.g. from washing steps or other fluid flow.

A large number of covalent attachment strategies suitable for coupling the LSL and the label SBM exist in the literature. For example, an amino group can be introduced into a label SBM through standard synthesis chemistries (such as is available from Genosys Biotechnologies, Inc. The Woodlands, Tex., USA). Chemistries to activate a LSL for covalent coupling to an amine-modified SBM include but are not limited to cyanogen bromide, N-hydroxysuccinimide or carbodiimide. AFFINITY CHROMATOGRAPHY by W. H. Scouten, 1981, John Wiley & Sons, and SOLID PHASE BIOCHEMISTRY, ANALYTICAL AND SYNTHETIC ASPECTs by W. H. Scouten, 1983, John Wiley & Sons) describe such activation techniques. In some cases, for example N-hydroxysuccinimide and carbodiimide, the LSL must contain surface carboxyl groups; for cyanogen bromide activation the LSL must contain surface hydroxyl groups. Well known hetero- and homo-bifunctional linkers might also be employed in such covalent conjugations. LSL particles with the appropriate chemical groups and diameter for use as LSL can be obtained from several commercial sources (for example, Bangs Laboratories, Inc., Carmel, Ind., USA). Covalent coupling of LSL to the label SBM may provide advantages in systems where stringent conditions are required to improve binding specificity because such conditions may interfere with the non-covalent adsorption of label SBM to a LSL.

Light Absorbing Materials

In one preferred aspect of the invention, a light absorbing material ("LAM") is added to the mixture of sample and label conjugate. The LAM is designed to prevent stray light from interfering in the light scattering reaction. Stray light arises primarily from microscopic imperfections in the reflecting interface and from scattering of the evanescent wave by particles that migrate to, but are not bound in, the penetration depth. The LAM, when dispersed in the bulk solution, absorbs and minimizes the effect of such stray light better than when such a material is coated onto a surface to form an paque layer (as in the prior art). The LAM should provide a final effective optical density ("O.D.") of at least 15; preferably more than 100; most referably 300 or more. An "effective" O.D. takes into account the wavelength of the incident light and is the O.D. at the wavelength of monochromatic light and the O.D. at the most prevalent wavelength of polychromatic light.

Suitable LAMs include the conjugate itself as well as numerous light absorbing dyes. Light absorbing dyes are any compounds that absorb energy from the electromagnetic spectrum, ideally at wavelength(s) that correspond the to the wavelength(s) of the light source. As is known in the art, dyes generally consist of conjugated heterocyclic structures, exemplified by the following classes of dyes: azo dyes, diazo dyes, triazine dyes, food colorings or biological stains. Specific dyes include: Coomasie Brilliant Blue R-250 Dye (Biorad Labs, Richmond, Calif.); Reactive Red 2 (Sigma Chemical Company, St. Louis, Mo.), bromophenol blue (Sigma ); xylene cyanol (Sigma); and phenolphthalein (Sigma). The Sigma-Aldrich Handbook of Stains, Dyes and Indicators by Floyd J. Green, published by Aldrich Chemical Company, Inc., (Milwaukee, Wis.) provides a wealth of data for other dyes. With these data, dyes with the appropriate light absorption properties can be selected to coincide with the wavelengths emitted by the light source.

Preferably, these LAMs do not interfere with the absorption of label SBM onto the LSL, or with the specificity of immobilized label SBM. For example, if the label SBM is a peptide, polypeptide or protein, the LAM preferably does not denature the peptide, polypeptide or protein. Similarly, if the label SBM is a nucleotide sequence, the LAM preferably does not denature the nucleotide sequence. Once selected on the basis of light absorption properties, the dyes can be evaluated empirically to ensure the dye does not interfere with the specific binding events required for implementation of the wave guide assay.

Surprisingly, the conjugate itself can also serve as a LAM. Using higher than necessary concentrations of label conjugate, for example, concentrations that provide an effective O.D. of at least 15, preferably more than 300, most preferably more than 500, has been found to improve detection as well. Methods of concentrating a conjugate include affinity purification or centrifugation as described in examples 2 and 3. While dyes may be used in conjunction with concentrated conjugate, it has been found that high concentrations of conjugates alone are usually sufficient. This phenomenon of adding more label to improve signal to noise levels is virtually unheard of in diagnostic assays and runs very much contrary to current thought.

While LAMs are an optional feature of the invention, their use results in the ability to use higher concentrations of label conjugate, higher intensities of light and larger label particles, all of which greatly improve performance over systems that do not contain a light absorbing material. The enhanced effect of using a LAM is presumably due to the elimination of stray light at a point much closer to its source than any known prior art method. Coatings on the waveguide surface opposite the reaction surface can only absorb stray light that reaches this surface. Stray light in the solution is still free to cause undesired scattering.

Methods of Use

Figure 1:
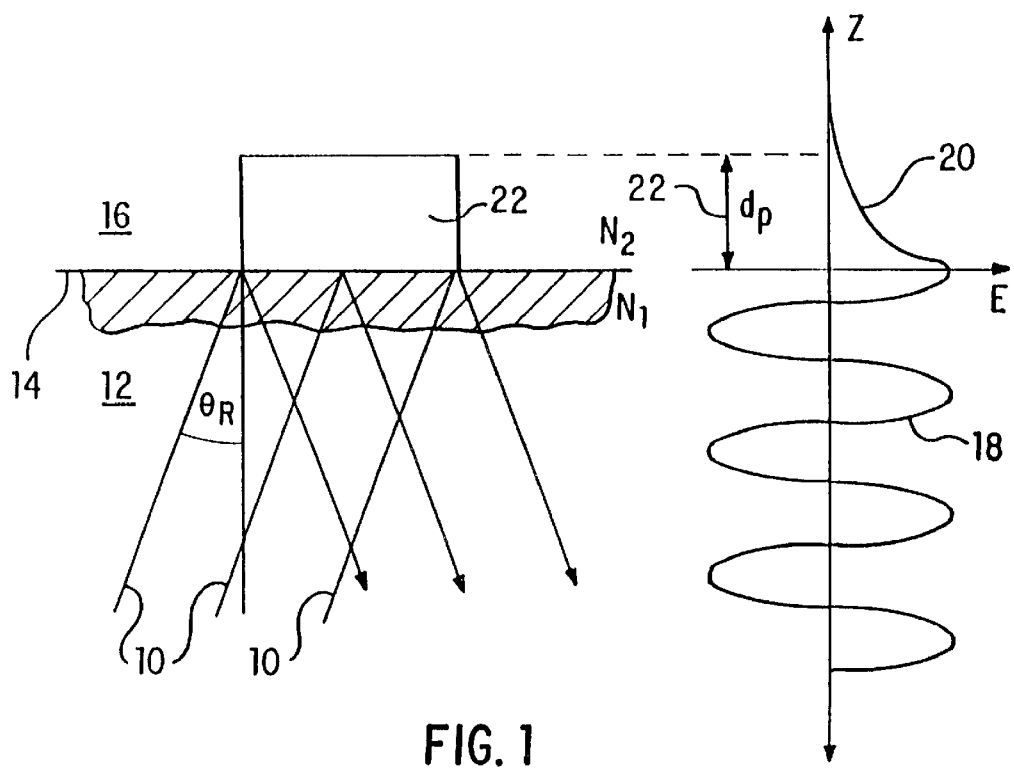
FIG. 1 illustrates the principles of total internal reflectance ("TIR") as known in the art, and is described in more detail in the background section. On the left.
Figure 3:
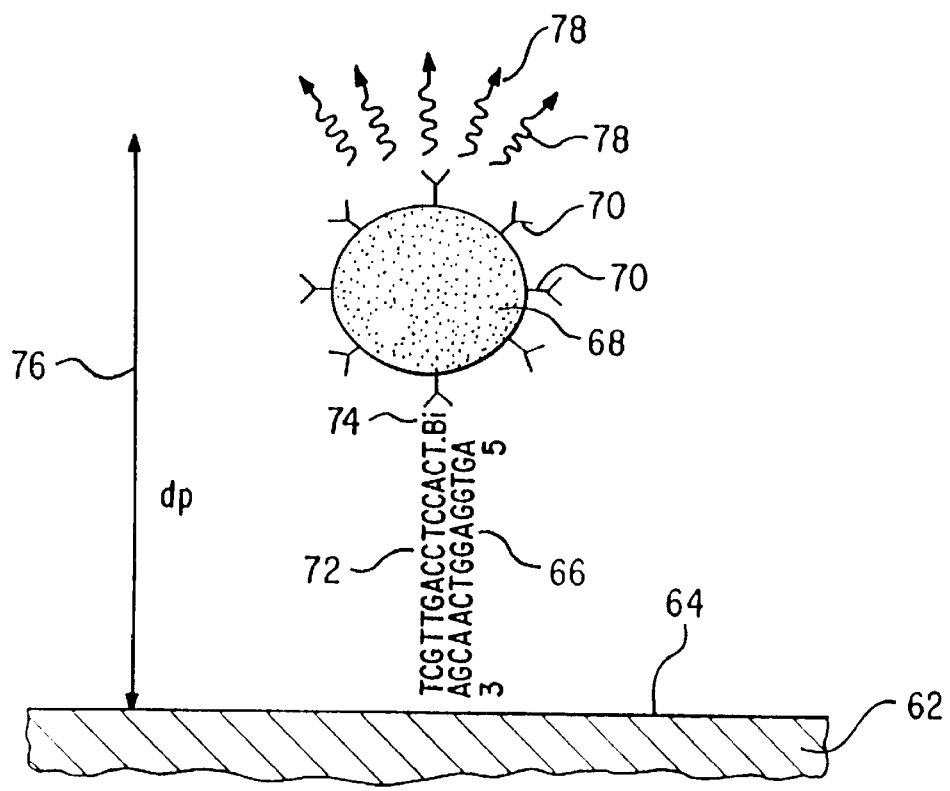
FIG. 3 is a diagrammatic representation of an embodiment of the invention where an oligonucleotide is immobilized on the waveguide surface and, within the evanescent wave penetration depth, captures a complementary oligonucleotide bearing a biotin moiety to which is attached a colloidal selenium light scattering particle.

Assay methods according to the invention employ TIR elements or waveguides as described above and include competitive and direct or indirect sandwich assay formats. An indirect sandwich format is depicted in FIG. 3.

First, a TIR element or waveguide 62 is prepared as discussed above, having at least one capture SBM immobilized at one or more sites in the reactive surface at the interface 64. The capture SBM is specific for the analyte. In FIG. 3, the SBM is a capture oligonucleotide, shown at 66, has the sequence 5'-AGTGGAGGTCAACGA (SEQ ID No. 3) and is immobilized at the interface 64. Preferably there are multiple SBMs immobilized to distinct sites that are spatially separated by non-situs portions.

In a sandwich format, fluid sample to be tested for the presence or amount of analyte is then brought into contact with the capture SBM on the reactive surface. The only general requirement of this process step is that the sample be in direct contact with the spatially separated immobilized SBMs to effect binding between analyte and the capture SBM. Mild mixing of the fluid sample after bringing it in contact with the reactive surface is also preferred in the process of the present invention, but is not required. Such mixing may help to ensure close contact between the fluid sample and the immobilized SBM. In lieu of mixing, a capillary flow of sample fluid across the reactive surface also promotes good contact and binding of analyte to the capture SBM.

Next, a label conjugate is also brought into contact with the reactive surface under binding conditions. The label conjugate binds to the analyte (or to a reporter group attached to the analyte) to form a light-scattering specific binding complex on or near the reactive surface. In the sandwich format the sample and conjugate may optionally be mixed prior to contacting the reactive surface with either component, or the two step process described may be used. If desired, the methods may be practiced using a LAM, which would be added to the conjugate or the sample-conjugate mixture.

Referring to FIG. 3, the label conjugate consists of the light scattering colloidal selenium particle 68 to which are immobilized antibiotin antibodies 70. The analyte is the oligonucleotide shown at 72 5'-TCGTTGACCTCCACT (SEQ ID No. 12) which has been labeled with a biotin ("Bi") reporter group 74. The complementarity of the oligonucleotides and the antibody specificity for biotin hold the LSL within the penetration depth 76 of the waveguide.

Numerous methods are known for incorporating such a reporter group into sample nucleic acid. For example, the sample might be amplified using a technique such as PCR or LCR, wherein the primers may bear the reporter. Alternatively, reporters can be coupled to individual nucleotide triphosphates which are then incorporated into extension products made from sample. This incorporation method a will work with PCR and also with the LCR variation known as Gap LCR.

The element is then illuminated in a manner to effect total internal reflection. Light sources and physical principles of TIR have already been described. In FIG. 3, the scattering of the evanescent wave is illustrated at 78. A slit is preferably used to reduce stray light. At the sites where light-scattering specific binding complexes have formed, the scattering of light is observed as lighter areas against the darker background of the non-situs portions (see, e.g. FIGS. 4–8A and 9–12). The brighter the situs appears, the more LSL is bound and the more analyte is present at that situs. The method can be used to quantitate or semi-quantitate by reading the gray tones into a computer and, using calibrators, estimating the amount of analyte present at each situs.

In a competitive format, the TIR device and reactive surface are as above. The LSL, however, is an analyte-analog which competes with sample analyte for the capture SBM. Thus, the brightness of the spot is inversely related to the quantity of analyte. In this format, the sample and conjugate must be mixed prior to contact of either one with the reactive surface. A LAM is useful in competitive formats, just as in sandwich formats.

It should be pointed out that the phenomenon variously known as "leading edge" or "shadowing" is not observed to be a problem with the present invention. This phenomenon is seen in chromatographic flow devices where binding of label at downstream sites is less than binding at upstream sites. This phenomenon is avoided principally because the factors that control binding of LSL are predominantly diffusion, not chromatography, even though some embodiments utilize a flow channel.

While it is possible to use the device of the invention by sequentially directing a light beam to individual sites and creating small loci of evanescent wave generation as in the prior art, it is decidedly more preferred to illuminate the entire waveguide at once, thereby creating evanescent wave energy across the entire reactive surface. This simultaneous illumination of the entire reactive surface is what enables simultaneous examination and comparison of all the sites, and thereby permits a far more rapid detection than was previously possible. A major advantage of the systems of the invention is that they permit real time binding and/or dissociation kinetics to be observed and allow for the development of a visible signal in a matter of seconds, e.g. from 1 to 20 seconds, in the preferred embodiment. The entire waveguide reactive surface can be seen (and/or detected) at once and it is all illuminated simultaneously, so the accumulation of LSL at a situs can be observed in real time since there is no need to scan each situs either for illumination with incident light or for detection of scattered light.

This finding is somewhat surprising in view of the prior teachings regarding TIR. Typically, the detectors of TIR elements are situated at the outlet of the element in order to gather the light as it exits the element. It has always been assumed that the light exiting the element was altered by the binding event. Indeed, detections using outlet light would not be possible without such a modification of the light by the binding events. Thus, one expects the light to be changed in some way by the binding event. In view of this, one could not guarantee the light would behave the same way upon encountering a second binding site and the teachings thus discourage multiple situs elements simultaneously illuminated by a common light source. The instant invention surprisingly finds that the internally reflected light at a downstream situs (with reference to light source) is not interfered with by binding events at an upstream situs.

Moreover, the degree or extent of binding can be monitored in real time as various conditions are changed. For example, where the SBMs are oligonucleotides allowed to form strand pairing and the changing condition is stringency, dissociation of the strands of nucleic acid (which results in freeing the LSL to the bulk solution where it cannot scatter evanescent wave energy) can actually be watched as a loss of the bright spot at the situs. As is known in the art, hybridization stringency can be controlled by varying parameters such as temperature and ionic strength. Increasing the temperature increases the stringency and destabilizes the duplex. Conventional heating blocks can be used for this technique and the preferred two-plate device described above can simply rest on the heating block. Oligonucleotide melt temperatures (Tm) can be obtained which exhibit good correspondence with solution phase melt temperatures. Stringency is also increased by decreasing the effective concentration of cations, such as by dilution with water. Thus, the waveguide and methods of the present invention provide a mechanism for real time monitoring of oligonucleotide melting temperatures. By controlling stringency in this manner, one can distinguish a perfectly complementary strand from one that contain even a single base mismatch. Such a system will find great utility in gene sequencing and in diagnostics.

Condition changes that affect antibody-hapten interactions can be evaluated in a similar fashion, substituting antibody and haptens for the oligonucleotide pairs. For example, increasing temperature will denature protein binding agents (e.g. antibodies), thus resulting in loss of binding ability. This denaturation of protein can be monitored in real-time using the invention. It should be recalled that any cognate bindng pairs utilized in holding the SBM to the waveguide surface, or in tying the LSL to the label SBM, should preferably withstand such altered conditions so that the binding of analyte to the capture SBM is the dissociation event monitored.

It should be noted that a further advantage of the present invention is that the reagents and sample, e.g. conjugate-sample solution, need not be washed off the capture site to allow detection. With fluorescent and radioactive labels, the unbound label must be removed from the surface to prevent unwanted signal. However, the unbound LSLs in the present invention generally diffuse away from the penetration depth and cease to give signal even without physical removal. Eliminating the need to wash unbound components from the surface contributes significantly to the speed with which an assay can be run.

In a unique reversal of the melt temperature determinations, the device and method of the invention can be used as a calibrated thermometer to monitor the precise temperatures of a waveguide, or as a manufacturing quality control to monitor the uniformity of heat transfer. As a thermometer, a series of oligonucleotide pairs of known incremental melt temperatures are placed in a series of situs on the reactive surface. As the temperature is increased, the pair with the lowest melt temperature will dissociate first, followed by subsequent pairs in order of their melt temperatures. The temperature of the reactive surface can be determined by knowing the melt temperatures of these calibrator oligonucleotides. A "ladder-like" effect is obtained if the oligonucleotide pairs are deposited in a linear array in order of their known melt temperatures.

Furthermore, the uniformity of heat transfer can be evaluated in a quality control setting if the entire waveguide is covered with ligonucleotides of identical melt temperatures. Dissociation should-occur instantaneously on all sites if heating is uniform. Such a chip can be used to determine is the heating block exhibits variations that lead to "hot spots" or "cold spots".

Detection of Scattered Light

As alluded to above, the scattered light may be detected visually or by photoelectric means. For visual detection the eye and brain of an observer perform the image processing steps that result in the determination of scattering or not at a particular situs. Scattering is observed when the situs appears brighter than the surrounding background (see, e.g., the Figures associated with examples). If the number of sites are small, perhaps a dozen or less, the processing steps can be effected essentially simultaneously. If the number of sites is large (a few hundred or more) a photoelectric detection systems is desired.

Photoelectric detection systems include any system that uses an electrical signal which is modulated by the light intensity at the situs. For example, photodiodes, charge coupled devices, photo transistors, photoresistors, and photomultipliers are suitable photoelectric detection devices. Preferably, the detectors are arranged in an array corresponding to the array of sites on the reactive surface, some detectors corresponding to non-situs portions. More preferred, however, are digital representations of the reactive surface such as those rendered by a charge coupled device (CCD) camera in combination with available frame grabbing and image processing software.

Some examples of the use of CCD cameras, frame grabber cards, computers and image processing software are found in co-pending, co-owned U.S. application Ser. No. 08/140,838, filed Oct. 21, 1993, which is incorporated herein by reference. Briefly, the CCD camera or video camera forms an image of the entire reactive surface, including all situs and non-situs portions, and feeds this image to a frame grabber card of a computer. The image is converted by the frame grabber to digital information by assigning a numerical value to each pixel. The digital system may be binary (e.g. bright=1 and dark=0) but an 8-bit gray scale is preferred, wherein a numerical value is assigned to each pixel such that a zero (0) represents a black image, and two hundred and fifty-five (255) represents a white image, the intermediate values representing various shades of gray at each pixel.

The digital information may be displayed on a monitor, or stored in RAM or any storage device for further manipulation. Two kinds of manipulation bear mentioning. First, the digitized data file may be converted and imported into a software drawing application. This will permit printing of the image for archival purposes, as was done with the video images generated in the examples to produce FIGS. 4–7, 8A and 9–12. A suitable drawing application is Publishers PaintBrush software (ZSoft Corp., Atlanta, Ga.); although many other software packages will accept or convert file imports in a wide variety of file formats, including "raw", TIFF, GIF, PCX, BMP, RLE, and many others. For printing and archival manipulations the conversions and importations should not alter the content of the data so as to result in a true and faithful representation of the image.

Secondly, image processing software may be used to analyze the digital information and determine the boundaries or contours of each situs, and the average or representative value of intensity at each situs. The intensity correlates positively with the amount of LSL present at the situs, and the amount of LSL present correlates (negatively or positively, depending on the assay format) to the amount of analyte binding member at such situs. This sort of data manipulation is evident in examples 2 and 5 and produced FIGS. 8B and 8C.

Multiple images of the same situs may be accumulated and analyzed over time. For repetitive images the waveguide or TIR element is either illuminated multiple times or, more likely, the lamp simply remains on until images are made at each desired time. By comparing light scattering at first time $t_1$, with the scattering at second time $t_2$, kinetic information can be obtained. This kinetic information is valuable especially when the assay is intended to be quantitative, since the time-dependency (i.e. rate) of the increase or decrease in the amount of light scattering may be more accurately indicative of the levels of the binding pair members present in the fluid sample than the total amount of scatter by the reaction at any given reaction point in time. Additionally, the use of multiple images can provide a data set over which the increase in scattered light detected is of a known function with respect to time. Measuring the rate of change of the intensity of scattered light from a given region of the reactive surface versus time provides a reaction rate. By using reaction kinetics, the rate is correlated to a quantitative measure of analyte concentration in the sample solution. Of course, data may be gathered at more than two times; generally the more data points obtained, the more reliable the kinetic or rate information.

An alternative method may be used instead of reaction kinetics. In this method one integrates the scattered light intensity versus time. The area obtained by this integration correlates to the concentration of the analyte in solution.

Various embodiments of the invention will now be shown by detailed example. The examples are illustrative only and are not intended to limit the invention.

EXAMPLES

Example 1 hCG Immunoassay using dye LAM

A. Binding of capture SBM to the waveguide

The waveguide used herein was an antibody coated standard glass cover slip commercially available from Corning (Corning, N.Y.; catalog #2, 22 mm sq.). The reactive surface was created on the glass waveguide by applying a small amount (approximately 2 μl) of an antibody solution (e.g., affinity purified goat polyclonal anti-βhCG, 10 mM phosphate, pH 7.4, 120 mM NaCl) to a delimited, roughly circular area. The stock antibody concentration was 3.3 mg/ml and could be used directly or the antibody could be diluted 1:10 into 1% sucrose (1% weight per volume [w/v] sucrose dissolved in water) before application. In either case, excess antibody was applied relative to the amount of protein that could be retained on the surface of the waveguide, and this excess antibody was washed off with water and allowed to dry.

Following immobilization of the antibody to the waveguide, the glass surface was treated with 0.05% alkaline-treated casein in water to block non-specific interactions between the glass surface and material in the fluid sample. A sufficient volume of the 0.05% casein solution to cover the surface was incubated at room temperature for 1–5 minutes and then the. glass was washed with water using a wash bottle. The casein coated the surface by physical adsorption and resulted in a surface that displayed "sheeting action", i.e., by careful application of the water stream, all water on the chip surface was removed by gravity flow.

B. Assembly of the device

A device for housing the assay reagents consisted of two glass cover slips as shown in FIGS. 2A–2C. One cover slip (the waveguide) contained the bound capture SBM and another glass cover slip created the channel to hold the sample-conjugate solution. The two cover slips were offset and held together by double-sided tape (Arcare 7710B, Adhesives Research Inc., Glen Rock, Pa.) so as to form a channel 16 mm wide and approximately 75 μm thick (the thickness of the double sided tape). The channel created holds approximately 25 μl in volume.

C. Illumination of the waveguide

The waveguide was then illuminated with a light source comprising a 150 watt incandescent bulb with a ca. 2 mm slit aperture. The waveguide was inserted into the light source slit so that light was shone into the 2 mm thick light receiving edge of the waveguide (see FIG. 2A). Although the waveguide was inserted into the slit at approximately 45° relative to the mask, no attempts were made to optimize the angle of incident light or to eliminate light hitting the element at less than the critical angle.

D. Addition of Sample, Light-Scattering Conjugate, Light Absorbing Dye

Next, a solution containing sample, a light-scattering conjugate, and a light absorbing dye was added to the reactive surface such that the capture situs was covered. The conjugate was prepared using a colloidal selenium particle (U.S. Pat. No. 4,954,452 to Yost, et al.) as follows: 1 ml of selenium colloid (32 O.D. concentration, at the absorption maximum wavelength of 546 nm) was mixed for 10 seconds with 2.5 μl of monoclonal anti-αhCG antibody (1 mg/ml, in PBS ) and 30 μl of 20% BSA (20 g/100 ml dissolved in water). Ten μl of the selenium conjugate was then added to 40 μl of hCG calibrator (hCG-Urine Controls from Abbott Laboratories (Abbott Park, Ill.; catalog #3A28-02)). Finally, 2 to 3 μl of blue McCormick food coloring dye (McCormick, Hunt Valley, Md.) was then added to this mixture, giving a final O.D. of 140–200 at 630 nm.

E. Detection of Light-Scattered Signal

Scattered light derived from the interaction of the evanescent light wave with the light-scattering label can be detected visually, or by means of a standard video analysis system. In the case of visual detection, a signal was observed in approximately 1 minute and becomes very visible within 5 minutes. This visual signal was recorded using a standard 8 bit CCD (charged coupled device) camera (Cohu model 4815 Cohu, Inc., San Diego, Calif.). A digital representation of the image was created using a frame grabber (Imaging Technology Incorporated, PC VISION plus Frame Grabber Board; Woburn, Mass.) in a Compac DeskPro 386/20e (Compaq Computer Corporation, Houston, Tex.). The digitized image data file was converted and imported into Publishers PaintBrush software (ZSoft Corp., Atlanta, Ga.) from which the image was printed on a 300 dpi resolution printer. The printed image is shown as FIG. 4.

Example 2

Improved hCG Waveguide Assay

A. Assay Configuration

The assay was run as described in example 1, however, the selenium conjugate was concentrated by a factor of 30× as follows. Ten ml of selenium colloid, 32 O.D. at 546 nM light, was mixed with 25 μl of anti-hCG antibody (1 mg/ml; described in example 1) and 300 μl of 20% BSA (see example 1). The resulting solution was placed into two 6 ml capacity centrifuge tubes and centrifuged using centrifuge model Centra-4B (International Equipment Company, Needham Heights, Mass.) at 5,000 R.P.M. for 10 minutes to pellet the selenium conjugate. About 9.66 ml of the supernatant, straw yellow in color, was removed so as to leave the selenium pellet, deep red in color, undisturbed. The selenium conjugate pellets were resuspended and combined in the remaining 0.33 ml of supernatant. The hCG "samples" were the hCG-Urine high positive, low positive and zero controls obtained from Abbott Laboratories (Abbott Park, Ill.; catalog #3A28-02) which contain, respectively, 250, 50 and 0 mIU/ml hCG. In addition, 0.5 ml of 10% casein (100 mM Tris, pH 7.4, 150 mM NaCl, 10% w/v casein) was added to each of the controls as a blocking agent to prevent non-specific binding, final casein concentration 0.9%. The waveguides were constructed as described in example 1, except the polyclonal anti-hCG antibody was applied to the glass surface with a glass capillary such that the situs was a hand-drawn "plus" symbol.

Equal volumes of 30× concentrated selenium conjugate (described above) and sample were mixed and immediately applied to the waveguide. In this case the optical density of the conjugate-sample mixture (approximately 465 O.D.) was so great that addition of the food coloring dye was not needed to prevent background scattering. In addition, the high concentration of conjugate increased both the sensitivity and speed of waveguide signal development, surprisingly without an increase in background scattering. The 0 mIU/ml sample gave no appreciable signal, the 25 mIU/ml sample (final concentration) gave a visible signal in about 30 seconds and the 125 mIU/ml sample (final concentration) gave a signal in 5 seconds or less. FIG. 5, imaged, digitized and printed as in example 1-D, shows a faint "plus" signal at 1 second for the high positive hCG sample (125 mIU/ml). Time=0 shows the waveguide channel filling with the conjugate solution; Time=1 seconds shows the initial, almost instantaneous formation of a visible plus signal; and Time=5 and 20 seconds shows a clearly visible plus signal.

B. Sensitivity Determination

Waveguide chips were made as above, however, a single spot of antibody solution (see example 1; polyclonal anti-hCG antibody at 1 mg/ml) was applied to the waveguide to form a single situs on the reactive surface. To estimate sensitivity in this system the experiment was repeated with 6 samples run at 0 mIU/ml and 5 samples run at 31 mIU/ml (nominal hCG concentrations, actual measurements were not carried out). The samples and conjugate were mixed for 1 minute, applied to the waveguide channel and a digital video image acquired after 1 minute of signal generation using a frame grabber and a CCD video camera. The digital images consist of a series of 8-bit grayscale values, ranging from 0 (dark) to 255 (white). The digital file thus consists of a series of such numbers and each number corresponds to a particular and unique pixel location of the image.

The resulting digitized data were analyzed using Image Pro Plus software (Media Cybernetics, Silver Spring, Md.) whereby a circular area, approximately the size of a signal spot was used to measure the numerical grayscale values of the image data. The digital values within the circular measuring area were averaged, i.e., each value within the circle was added and the resulting sum divided by the number of such values. Such values were obtained for the capture situs and for a representative background, non-situs portion adjacent to the signal situs. The difference, signal minus background, constituted the measured value. The data obtained for this experiment is shown in Table 2.1:

TABLE 2.1

| | 0 mIU/ml | | | 31 mIU/ml | |
|---|---|---|---|---|---|
| Signal | Background | Net Signal | Signal | Background | Net Signal |
| 50.9 | 44.8 | 6.1 | 69.6 | 50.2 | 19.4 |
| 51.6 | 44.6 | 7.1 | 78.4 | 54.7 | 23.7 |
| 50.6 | 44.1 | 6.4 | 112.4 | 77.0 | 35.6 |
| 64.1 | 58.6 | 5.6 | 102.3 | 64.2 | 38.1 |
| 66.2 | 58.7 | 7.5 | 105.7 | 76.0 | 29.7 |
| 54.8 | 48.0 | 6.8 | | | |
| | | mean: 6.6 ± 0.7 | | | mean: 29.2 ± 7.8 |

The mean net signal for the 0 mIU/ml experiment is 6.6±0.7 mIU/ml and for the 31 mIU/ml experiment, 29.2±7.8 mIU/ml. Hence, by linear interpolation, 1 gray level=1.4 mIU/ml and a net signal value equal to 2 standard deviations above the 0 mIU/ml net signal, i.e. 1.4, yields a sensitivity estimate of about 2 mIU/ml.

Example 3

Thyroid Stimulating Hormone (TSH) Immunoassay
A. Bind capture reagent to the solid phase A waveguide was prepared as described in example 1, except the antibody capture situs was created on the glass surface of the waveguide by applying a small amount (approximately 2 $\mu$l) of an antibody solution composed of affinity purified polyclonal anti-$\alpha$TSH antibody at a concentration of 0.25 to 0.5 mg/ml. The antibody solution contains 1% sucrose. The antibody was allowed to dry and thereby became immobilized and was adsorbed onto the glass surface, rinsed with HPLC water and forced air dried. Following immobilization, the glass surface is treated for $\leq$1 minute with 0.05% alkaline treated casein (100 mM Tris, pH 7.8, 150 mM NaCl) to block non-specific interactions between the reactive surface and material in the fluid sample; and to promote flow through the channel. The excess casein is rinsed off the slide with HPLC water in a "sheeting action". Any remaining liquid is dried by forced air.

The disposable was assembled as described in example 1 and was placed in the slit aperture of the light source as described in example 1.
B. Addition of Sample and concentrated light-scattering conjugate Next, a solution containing sample and a light scattering conjugate was added to the reactive surface such that the capture situs was covered. Light scattering conjugate was prepared by labeling a second antibody (monoclonal anti-$\beta$TSH; 10 $\mu$g/ml) with selenium colloid of example 1 diluted to 16 O.D. (absorption maximum wavelength of 546). After mixing for 10 seconds, the conjugation was blocked with 0.6% BSA and spun at 8000 rpm for 3–5 minutes to concentrate. The conjugate was resuspended in $\frac{1}{20}$th its original volume. Next, 15 $\mu$l of sample buffer, which consisted of 7.5 $\mu$l of selenium conjugate mixed with 7.5 $\mu$l of 10% alkaline-treated casein (100 mM Tris, pH 7.8, 150 mM NaCl) to give a final casein concentration of 2.5%, was mixed with 15 $\mu$l of TSH sample. The TSH samples were the IMx® Ultrasensitive hTSH Assay calibrators A–F obtained commercially from Abbott Laboratories (catalog #A3A62-01) and having TSH levels as follows: A=0, B=0.5, C=2, D=10, E=40, and F=100 $\mu$IU/ml. These calibrators were used at a 1:1 dilution with the sample buffer, giving a final concentration of half that stated as the calibrator's concentration.
C. Detention of Light-Scattered Signal scattered light derived from the interaction of the evanescent light wave with the light-scattering label was detected visually and by means of a standard video analysis system (see e.g., example 1). In the case of visual detection, a signal was observed in approximately 1 minute. FIG. 6 was imaged digitized and printed as in example 1-D. As shown in FIG. 6, a signal above background is clearly observed in 1 minute. The estimated sensitivity of the system with visual detection is 0.25 $\mu$IU/ml TSH. Signal at 0.125 $\mu$IU/ml TSH is barely visible by eye and distinguishable above zero.

Example 4

DNA Hybridization Assay
DNA Waveguide Construction

DNA waveguides for the detection of human genetic mutations that cause cytic fibrosis were constructed from glass substrates 1 cm square. Oligonucleotides were immobilized to the glass to provide multiple capture sites in the reactive surface. In particular, nine different oligonucleotides, designated CAT01 through CAT09 (SEQ ID Nos. 1–9) were applied to the glass surface of the waveguide to form a 3×3 array pattern such that the CAT# corresponded to the position occupied by the same number on a standard touch-tone telephone. DNA spots were about 2 mm in diameter and about 2 The sequence and mutation site of CAT01 through CAT09 (SEQ ID Nos. 1–9) are shown in Table 4.1.

TABLE 4.1

| SEQ ID No. | Oligo Designation | Sequence 5'- - - - - - - to - - - - - - - 3 | Mutation Designation |
|---|---|---|---|
| 1 | CAT01 | TATCATCTTTGGTGT-NH$_2$ | $\Delta$508 WT |
| 2 | CAT02 | AATATCATTGGTGTT-NH$_2$ | $\Delta$508 |
| 3 | CAT03 | AGTGGAGGTCAACGA-NH$_2$ | G551D WT |
| 4 | CAT04 | AGTGGAGATCAACGA-NH$_2$ | G551D |
| 5 | CAT05 | AGGTCAACGAGCAAG-NH$_2$ | R553X WT |
| 6 | CAT06 | AGGTCAATGAGCAAG-NH$_2$ | R553X |
| 7 | CAT07 | TGGAGATCAATGAGC-NH$_2$ | G551D + R553X |
| 8 | CAT08 | TGGAGATCAACGAGC-NH$_2$ | G551D + R553X WT |
| 9 | CAT09 | TGGAGGTCAATGAGC-NH$_2$ | G551D WT + R553X |

The human genetic mutations are indicated by standard notation. For example, $\Delta$508 indicates a 3 base pair deletion at position 508 of the cystic fibrosis transmembrane conductance regulator polypeptide (J. Zielenski, et al. *Genomics* 10:214–228, 1991). The "WT" indicates the wild type or normal sequence at this position. The presence of the amino group at the 3' end of the oligonucleotide facilitates immobilization of the DNA to the surface of the waveguide, however, the mechanism is not presently known. The DNA solutions were prepared by Synthecell (Columbia, MD) and were diluted 1:20 into PBS (phosphate buffered saline, pH 7.4) buffer and applied to the glass surface of the waveguide using the blunt end of a drill bit approximately 1 mm in diameter. DNA was immobilized on a clean glass surface or to a glass surface previously coated with 0.05% casein; hybridization results were indistinguishable. The final concentrations of DNA applied to the glass surface of the waveguide ranged from a high value of 14 $\mu$M for CAT02 to a low of 0.9 $\mu$M for CAT08 and was determined by comparison to the concentration of starting material received from Synthecell. After application, the DNA solutions were allowed to dry on the chip at room temperature or, on humid days between about 35% and 80% relative humidity, in an incubator set at 50°–70° C. until dry (about 10 minutes). This procedure formed nine "spots" or hybridization capture sites in the 3×3 array described above.

B. Hybridization

To evaluate DNA waveguide performance, nine additional oligonucleotides, CAT21B through CAT29B (SEQ ID Nos. 10–18) were synthesized by Synthecell with a biotin label on the 3' end. The sequences of the test DNA oligonucleotides are listed in Table 4.2.

TABLE 4.2

| SEQ ID No. | Oligonucleotide Designation | Sequence 5' - - - - - - - - to - - - - - - - - 3 |
|---|---|---|
| 10 | CAT21B | ACACCAAAGATGATA-biotin |
| 11 | CAT22B | AACACCAATGATATT-biotin |
| 12 | CAT23B | TCGTTGACCTCCACT-biotin |
| 13 | CAT24B | TCGTTGATCTCCACT-biotin |
| 14 | CAT25B | CTTGCTCGTTGACCT-biotin |
| 15 | CAT26B | CTTGCTCATTGACCT-biotin |
| 16 | CAT27B | GCTCATTGATCTCCA-biotin |
| 17 | CAT28B | GCTCGTTGATCTCCA-biotin |
| 18 | CAT29B | GCTCATTGACCTCCA-biotin |

The oligonucleotides were designed and named such that CAT21B (SEQ ID No. 10) is complementary to CAT01 (SEQ ID No. 1), CAT22B (SEQ ID No. 11) is complementary to CAT02 (SEQ ID No. 2), et cetera to CAT29 (SEQ ID No. 18) which is complementary to CAT09 (SEQ ID No. 9). The concentrations varied from a high of 473 mM for CAT25B (SEQ ID No. 14) to a low of 151 mM for CAT27B (SEQ ID No. 16). Each of the nine DNA samples were diluted 1 $\mu$l into 1 ml of hybridization buffer (1% casein, 10 mM Tris pH 7.4, 15 mM NaCl), and a different one was applied to each of the nine different DNA waveguides and incubated at room temperature (approximately 23° C.) for 5 minutes. The surface of the DNA waveguides were washed with PBS using a wash bottle and then stored under PBS until detection of hybridization.

C. Detection of Hybridization

Hybridization of the nine different biotin labeled DNA's was detected in the waveguide by light that was scattered from a selenium anti-biotin conjugate. The selenium conjugate was prepared by addition of 2.5 $\mu$l of anti-biotin (polyclonal rabbit anti-biotin antibody, 1.13 mg/ml in PBS, pH 7.4—see EP 0 160 900 B1 to Mushahwar, et al., corresponding to U.S. Ser. No. 08/196,885) to 1 ml of selenium colloid (32 O.D. concentration) from example 1, followed by addition of 30 $\mu$l of bovine serum albumin (powder BSA dissolved in water to give a 20% w/v solution). Fifty $\mu$l of the conjugate solution was applied to the surface of the DNA waveguide and light directed into the side of the waveguide to observe binding of selenium to the various DNA capture sites. Positive hybridization was visible at many sites within 1 minute. The DNA waveguides were washed with PBS to remove excess selenium conjugate, illuminated to effect waveguide excited light scattering, and imaged using a Cohu model 4815 CCD camera. The image was digitized and printed as in example 1-D, and is shown in FIG. 7. The entire pattern of DNA hybridization was detected using the waveguide in a single image measurement and allowed determination of the DNA sequence of the oligo applied to the waveguide. In the case of CAT21B (SEQ ID No. 10) and CAT22B (SEQ ID No. 11) (first two frames of FIG. 7), the hybridization pattern was relatively simple because there was negligible sequence homology of these oligonucleotides with DNA capture sites other than CAT0 (SEQ ID No. 1) and CAT02 (SEQ ID No. 2), respectively. In the case of CAT23B-CAT29B (SEQ ID Nos. 12–18), however, significant sequence homology results in a more complicated binding pattern.

Example 5

Real Time DNA Melting

A. DNA Waveguide Construction

Waveguides containing two DNA capture spots were made by applying 1 $\mu$l of an oligonucleotide solution containing CAT03 (SEQ ID No. 3) and CAT04 (SEQ ID No. 4; 1:20 dilution into PBS) to the waveguide cover slip (coated with 0.05% casein as in example 1) followed by drying at room temperature. Excess DNA was rinsed from the two spots with water and then the chips were dried at room temperature. The DNA waveguide with two spots was joined to another glass cover slip to form a disposable for housing the assay reagents as in example 1.

B. Hybridization and Detection

A solution of either CAT23B (SEQ ID No. 12) or CAT24B (SEQ ID No. 13) was prepared by diluting 1 $\mu$l into 1 ml of 1% casein, 10 mM Tris, pH 7.4, 15 mM NaCl. The solution was introduced into the channel of the waveguide disposable by capillary flow and hybridization allowed for a period of 5 minutes at room temperature. The DNA solution was displaced from the channel by introduction of a selenium conjugate (example 4) and the waveguide was placed in the light source to effect detection. Within seconds, two bright spots appeared at the DNA capture sites indicating hybridization had occurred. Hybridization between CAT23B (SEQ ID No. 12) and CAT03 (SEQ ID No. 3) was expected as was hybridization between CAT23B (SEQ ID No. 12) and CAT04 (SEQ ID No. 4) because the difference between CAT23B (SEQ ID No. 12) and CAT04 (SEQ ID No. 4) was only a single base pair. At conditions of low temperature (i.e., room temperature) and high salt .(15 mM NaCl), there was not sufficient discrimination in the hybridization process to distinguish a single base mismatch.

C. Real Time Melting

Figure 8A:
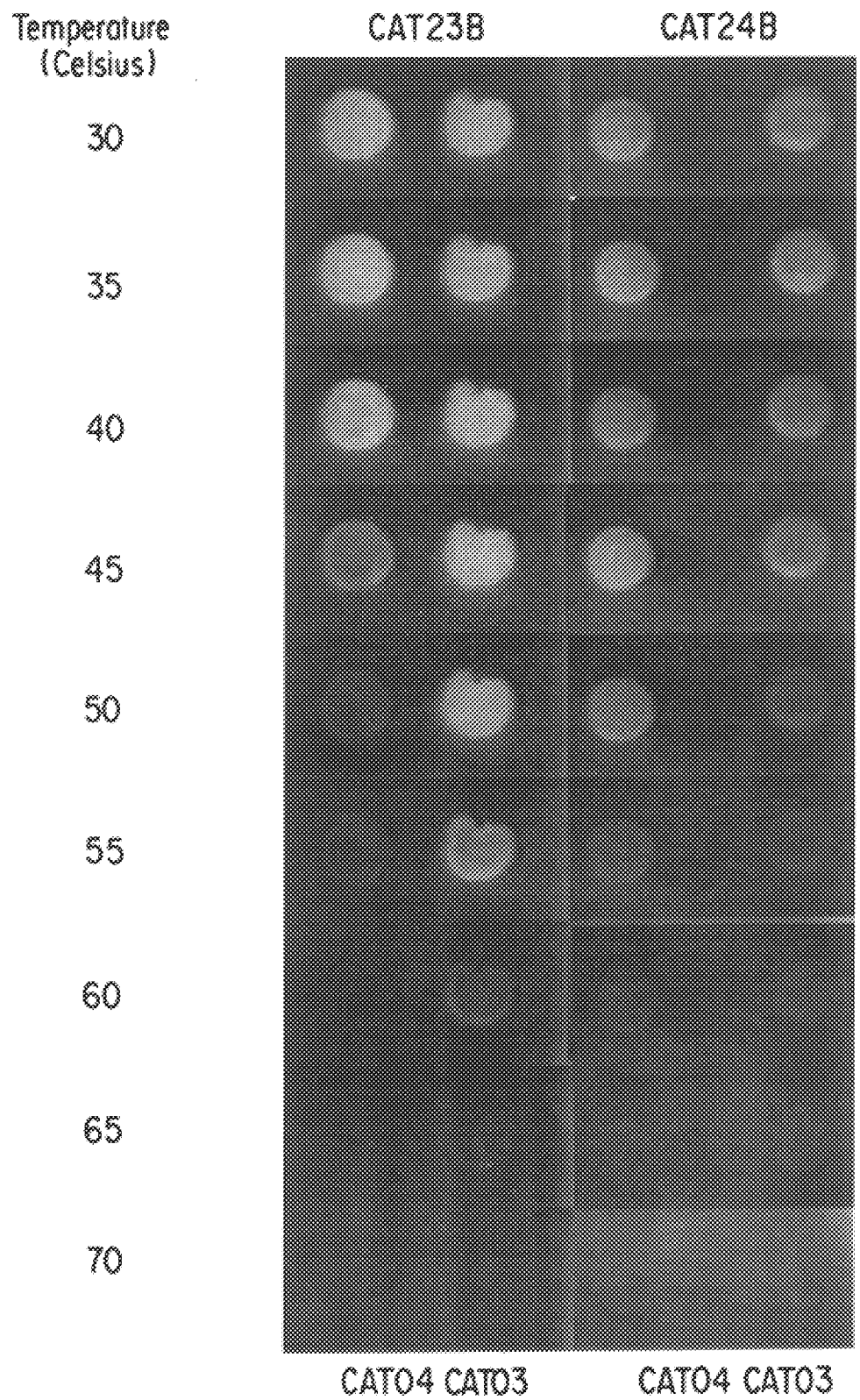
Figure 8B:
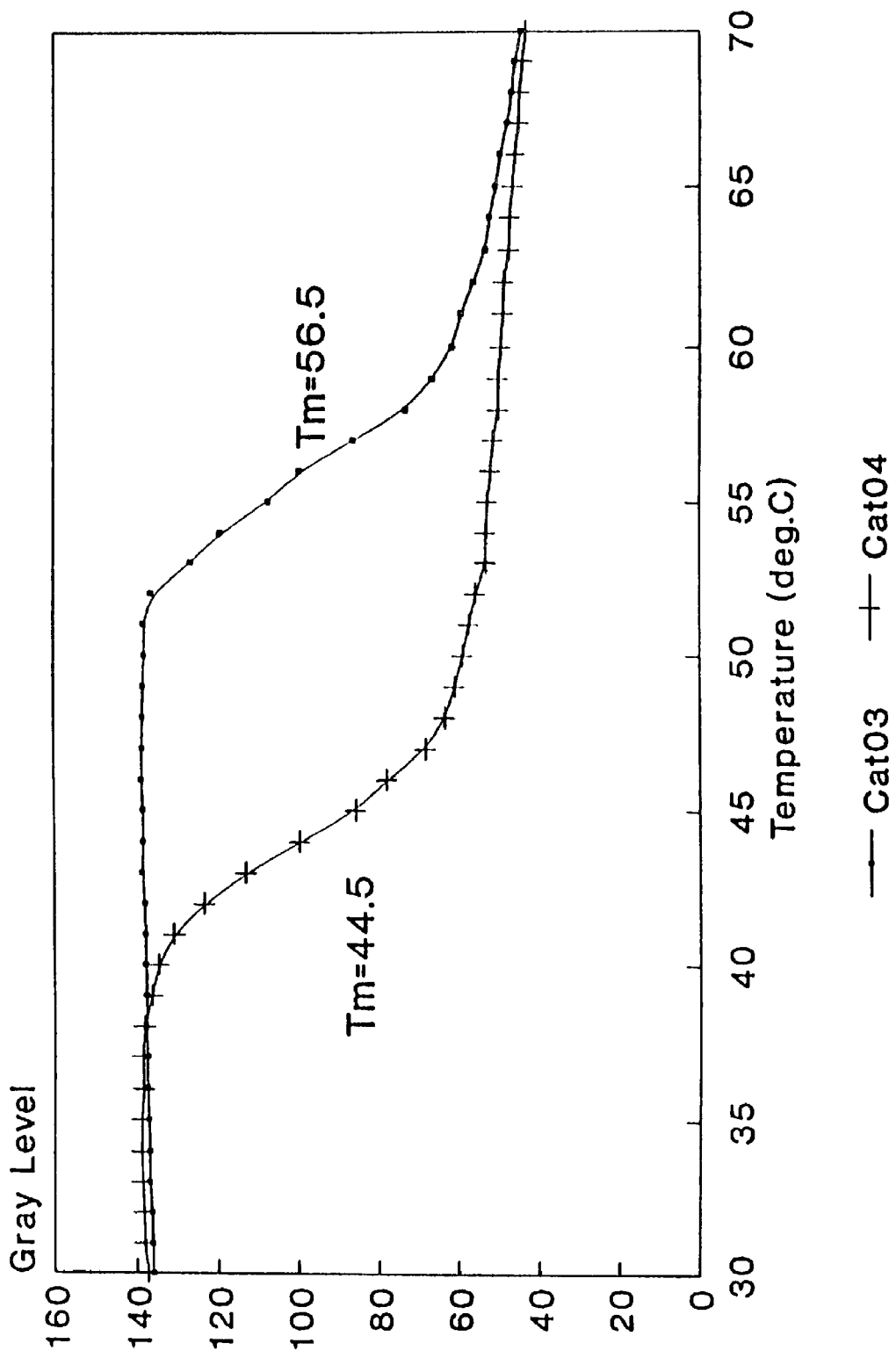
FIGS. 8B and 8C are DNA dissociation or melting curves. At each temperature is plotted the mean intensity data generated in example 5 for that temperature.
Figure 8C:
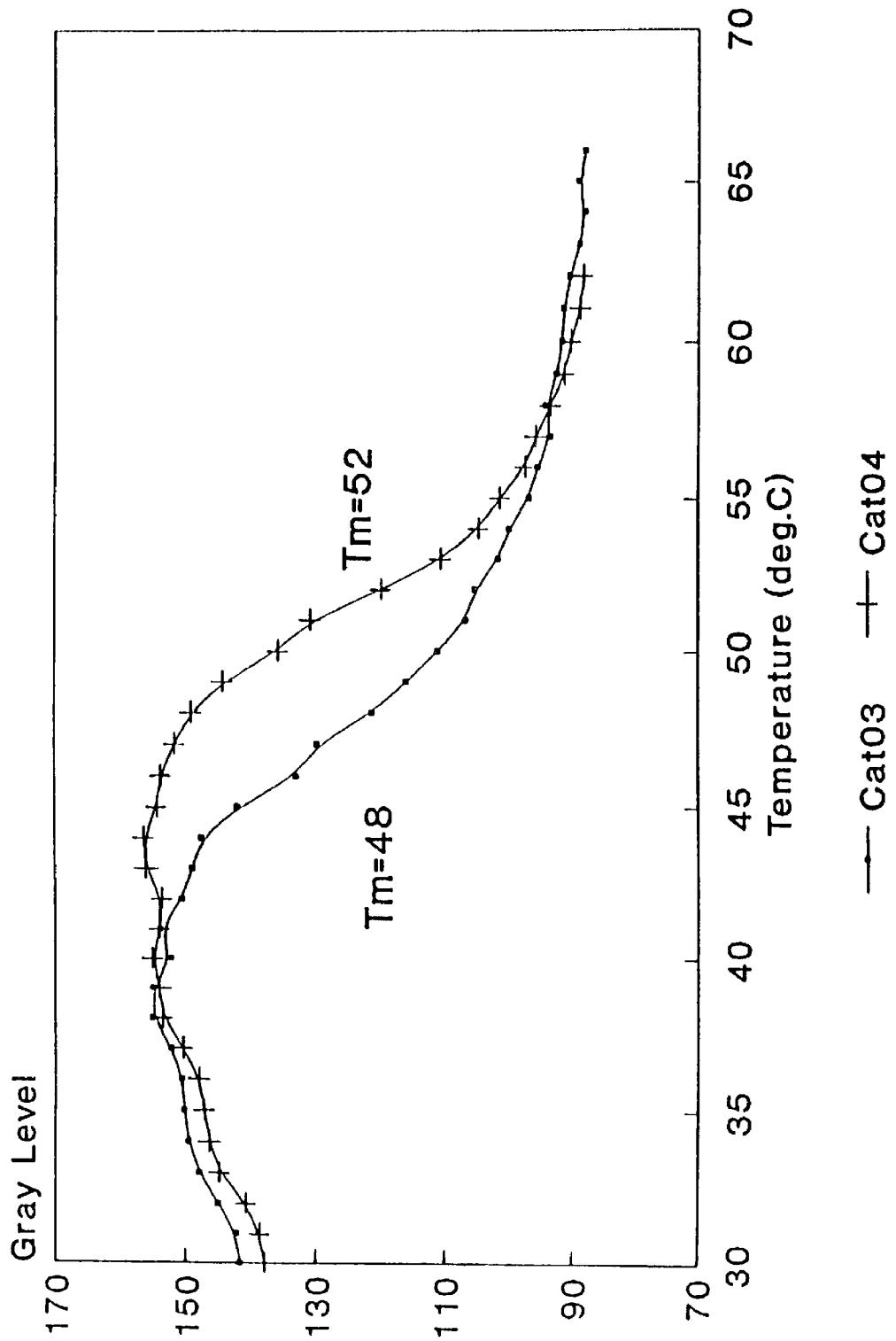
Figure 9A:
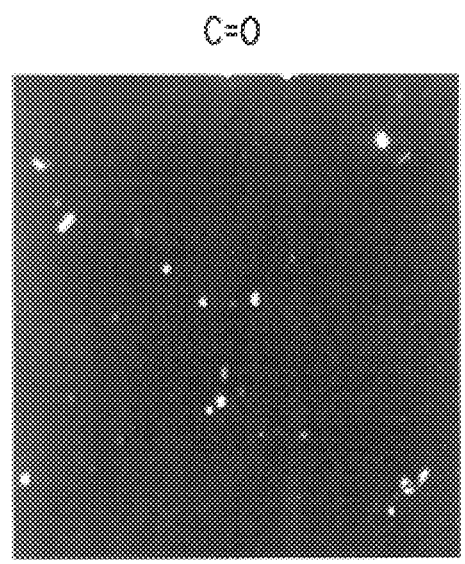
Figure 9B:
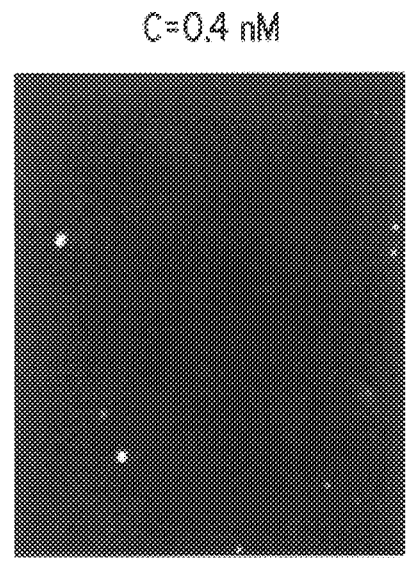
Figure 9C:
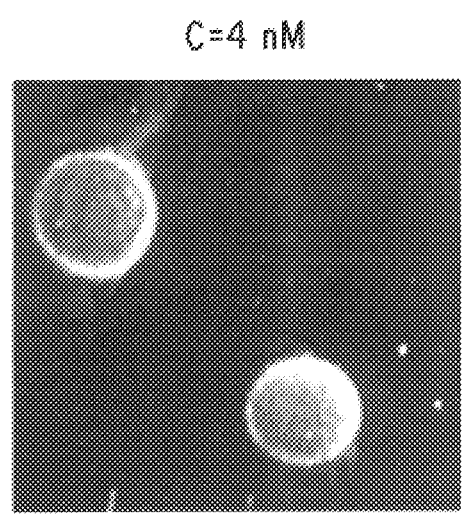
Figure 9D:
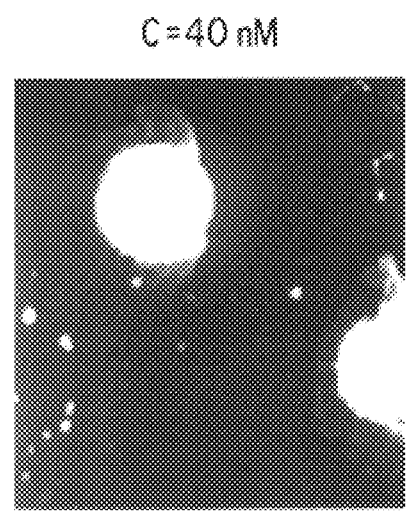

After observation of the room temperature hybridization pattern, the temperature of the DNA waveguide was increased using a heating block applied to the non-waveguide side of the channel (i.e., the second glass cover slip used to create the channel of the disposable). The effect of heat on the hybridization pattern was recorded in real-time using a CCD camera and a Video Cassette Recorder (VCR) focused on the waveguide surface. The temperature of the heating block under the waveguide (i.e., in contact with the second glass cover slip used to create the channel of the disposable) was measured using a thermocouple. A digital temperature readout (Watlow, series 965 temperature controller, Watlow Controls, Winona, Minn.) was recorded by imaging with the CCD camera. As temperature increased, the intensity of the DNA sites decreased as expected from DNA melting. In addition, the DNA sites containing the mismatched hybridized DNA melting at lower temperatures than the sites which contained the exact match DNA. As a result, it was possible to distinguish between exact match and single base mismatch hybridization and thereby allow detection of single base mutations. Data, in the form of video images, was collected at every 1° C. increment and was digitized using the frame grabber as before. FIG. 8A is the printed representation of the data at 5° C. intervals, which shows that by about 50° C. the mismatched spots begin to fade but the perfectly matched pairs remains visible until about 60° C. The intensity of the capture sites was measured as in example 2 and the mean spot intensity was calculated for each temperature. FIG. 8B is a melting curve plot for CAT23B (SEQ ID No. 12) and FIG. 8C is a melting curve plot for CAT24B (SEQ ID No. 13). Melt temperatures are estimated as the point halfway between the top and bottom plateaus.

Example 6

DNA Hybridization Assay Sensitivity

Sensitivity of the waveguide DNA hybridization assay was estimated by observing scattering signal intensity as the concentration of DNA applied to the waveguide was reduced. Four identical DNA waveguides were made by applying 0.5 µl of CAT01 (SEQ ID No. 1) and CAT03 (SEQ ID No. 3), which were diluted separately 1:20 in PBS. This procedure was repeated 2 times to form a 2×2 array with CAT01 (SEQ ID No. 1) at the upper-left and lower-right corners (as viewed) and with CAT03 (SEQ ID No. 3) at the upper-right and lower-left corners (as viewed). The DNA spots were dried in a 70° C. oven for 15 minutes and, without washing off excess DNA, a second cover slip was affixed to form a channel as in example 1. CAT23B DNA (SEQ ID No. 12) was diluted into hybridization buffer (1% casein, 10 mM Tris, pH 7.4, 15 mM NaCl) to give concentrations of 39.6 nM, 4 nM and 0.4 nM. Hybridization buffer only was used as the fourth concentration of DNA (0 nM). Thirty µl of each DNA solution was introduced to one of the four waveguide devices. The DNA solution was applied to the open gap at one end of the waveguide disposable and the channel was subsequently filled by capillary action. The solutions were incubated at room temperature for 10 minutes to allow hybridization to occur. Next, 30 µl of selenium anti-biotin conjugate (example 4) was applied to one end of the channel and a paper towel applied to the opposite end of the channel to remove the DNA solution and, by displacement, fill the channel with conjugate solution. The hybridization was detected by illumination of the DNA waveguide while the channel was filled with conjugate solution. After one minute of selenium conjugate binding, a digital image of the waveguide signal was acquired using a Cohu CCD camera at 30 frames per second. The imported and printed image of each of the four chips is shown in FIG. 9. Specific hybridization was indicated by the presence of signal only at the CAT03 (SEQ ID No. 3) sites. There was no signal from any situs on the chip with 0 nM sample and no signal from the CAT01 (SEQ ID No. 1) sites at any concentration. The lowest concentration of DNA used in the experiment, 0.4 nM CAT03, was detected by the waveguide under these conditions and represents an approximate measure of sensitivity. As a typical comparison, Pease, et al., *Proc. Natl. Acad. Sci.*, 91: 5022–5026, 1994report detecting a 10 nM concentration of fluorescent labeled DNA in conjunction with a laser-scanning system in a read time of minutes instead of 1/30 of a second.

Example 7

Detection of High Site-Density DNA Waveguide

A high site-density (defined as the number of sites/chip, in distinction from the amount of DNA per situs) DNA waveguide was created by multiple applications of a single oligonucleotide, CAT01 (SEQ ID No. 1). An Asymtek Automove 102 XYZ Table (Asymtek, Carlsbad, Calif.) was programmed to dip a 150 µm diameter pin into a solution of CAT01 DNA (1:20 dilution of CAT01 into PBS) and then touch the pin to the surface of a casein coated, 1 cm square glass waveguide. The process was repeated 323 times to form an 18×18 array of DNA spots 150 µm in diameter spaced 300 µm apart (the 18×18 array should have 324 spots, however, a programming error omitted placement of one spot resulting in an a "hole" in the upper right (as viewed) portion of the array and, hence, 323 spots). The entire array occupied a square of approximately 5.1 mm per side, (26 mm$^2$) in the center of the 1 centimeter square waveguide.

Figure 10:
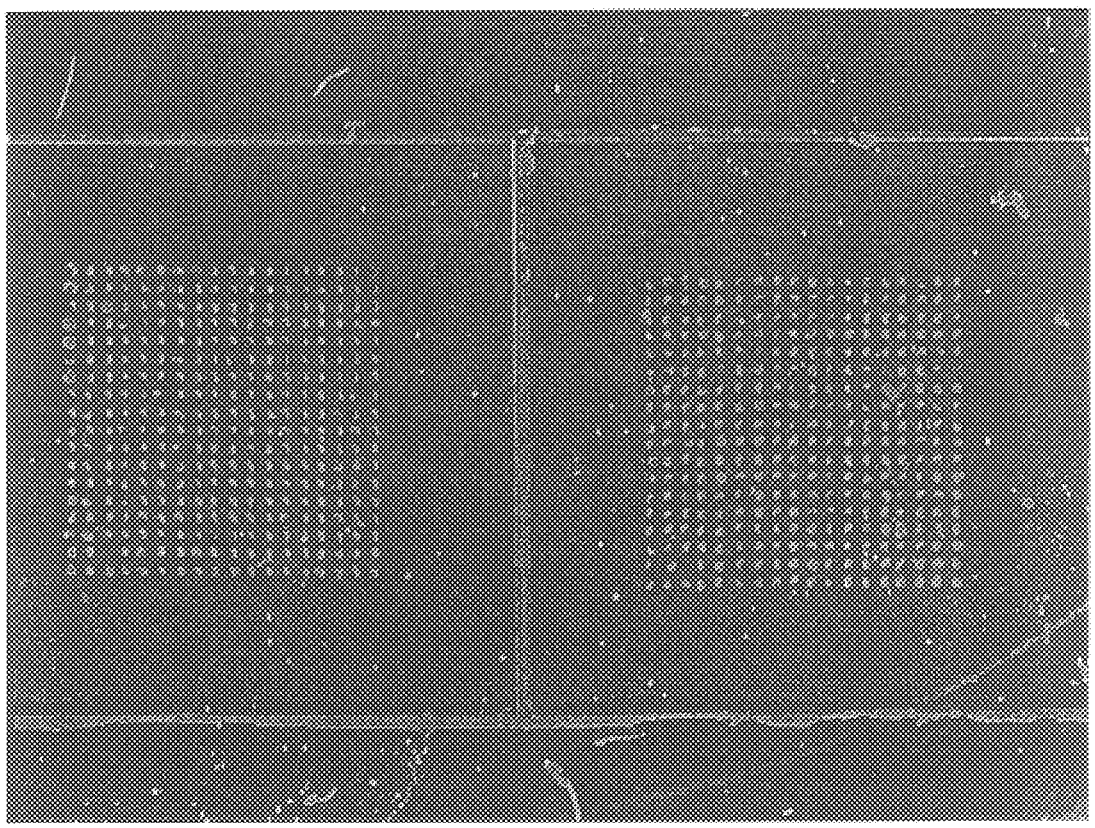
Figure 11A:
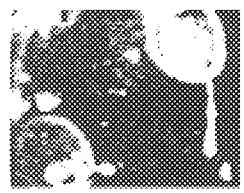
Figure 11B:
Figure 11C:
Figure 11D:
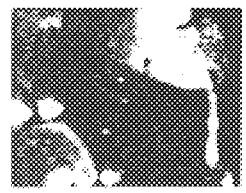
Figure 11E:
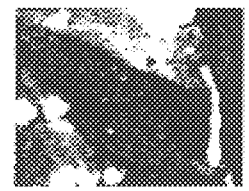
Figure 11F:

The resulting waveguides were dried, washed with water and dried again in preparation for hybridization. Hybridization was carried out by placing a solution of CAT21B (SEQ ID No. 10) diluted 1:1000 in 1% casein, 10 mM Tris, pH 7.4, 15 mM NaCl on the surface of the waveguide so as to cover the entire array for 5 minutes at room temperature. The DNA solution was rinsed from the surface of the waveguide using PBS and then hybridization was detected by covering the surface of the waveguide with selenium anti-biotin conjugate (example 4) and illuminating the waveguide. Hybridization of the CAT21B DNA (SEQ ID No. 10) to the DNA array could be observed visually in approximately 30–60 seconds. The excess conjugate solution was washed away by placing the chip in a dish of PBS. The hybridization pattern was recorded by digitization of a video image using a frame grabber as before. A printed representation of the image data is shown in FIG. 10. As can be seen, the waveguide detection allowed simultaneous measurement and differentiation of all 323 hybridization sites.

Example 8

Dissociation of Hybridized DNA by Low Ionic Strength

Another advantage of waveguide detection is reusability. In this case the sample DNA hybridized to a surface of the waveguide must be stripped from the chip without harming the DNA fixed to the surface. This example demonstrates the utility of the waveguide to monitor the regeneration process.

Cystic fibrosis DNA waveguides bearing oligonucleotides CAT01 through CAT09 (SEQ ID Nos. 1–9) in a 3×3 array were constructed as described in example 4 using a 22 mm square #2 glass cover slip. A flow channel was formed by affixing a second cover slip to the waveguide using silicone adhesive (Dow Corning, Midland, Mich.) and two pieces of tubing at opposite diagonal corners to provide an inlet and outlet. The coverslips were offset as described in example 1 to allow injection of light into the upper coverslip which functioned as the waveguide. A solution of CAT23B ((SEQ ID No. 12) which is perfectly complementary to CAT03

(SEQ ID No. 3)) in hybridization buffer (1% casein in 10 mM Tris, pH 7.4, 12 mM NaCl) was manually pumped into the flow channel using a syringe; flow was stopped and hybridization was carried out for 1 minute. Next a solution of selenium anti-biotin conjugate (example 4) was pumped into the channel displacing the DNA solution; flow was stopped; and hybridization was detected by waveguide illumination in the presence of conjugate (as before). Next the channel was washed by pumping in PBS to displace the conjugate solution. Finally, the hybridized DNA-selenium anti-biotin conjugate complex was dissociated from the surface of the waveguide by pumping pure water into the channel. The water increases the stringency conditions by diluting out the NaCl to decrease the ionic strength. The dissociation of the DNA and selenium from the capture sites was observed in real-time and recorded using a video camera and a VCR. At various times of the dissociation process the video image was captured using a frame grabber, digitized and printed as before, and the results are shown in FIG. 11. Because of excessive air bubbles in the flow chamber, only the upper right 2×2 array is shown; e.g. four sites corresponding to numerals 2 (CAT02, SEQ ID No. 2), 3 (CAT03, SEQ ID No. 3), 5 (CAT05, SEQ ID No. 5) and 6 (CAT06, SEQ ID No. 6). As can be seen, the process of dissociation was followed from the initial introduction of low ionic strength medium to the final removal of substantially all waveguide signal from the DNA chip. Hence, the waveguide allowed the operator to monitor the regeneration process of the DNA waveguide for re-use. In particular, real time information on the regeneration can be used to control the regeneration time and thereby improve processing times in a diagnostic application.

Example 9

Multiplex Antibody Test for DNA

A multiplex antibody test for bi-haptenated DNA products was created using a common biotin SBM and a different "capture" SBM unique for each of the 3 oligonucleotide products. Such bi-haptenated oligonucleotides are representative of products obtained by a multiplex ligase chain reaction as is disclosed in U.S. Ser. No. 07/860,702 filed Mar. 31, 1992, published as WO 93/20227 (Abbott Labs). The waveguide was constructed by immobilizing anti-fluorescein, anti-adamantane, and anti-quinoline monoclonal antibodies to a Corning #2 glass microscope cover slip. Anti-adamantane antibodies are disclosed in U.S. Ser. No. 808,508 filed Dec. 17, 1991 and in PCT/US93/05534. Anti-quinoline antibodies are disclosed in U.S. Ser. No. 07/858,820 filed Mar. 27, 1992, published as WO 93/20094. All these documents are incorporated herein by reference.

Figure 12A:
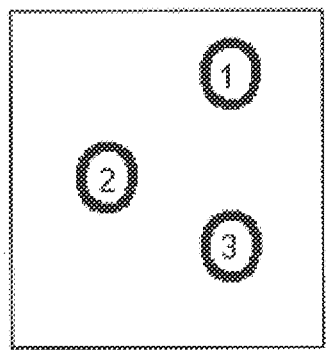

The antibodies were diluted 1:10 in water and approximately 0.5 µl applied to the waveguide, forming 3 spatially separated spots as shown in FIG. 12a with anti-fluorescein at the upper right apex (spot #1), anti-adamantane at the left (spot #2) and anti-quinoline at the bottom-right (spot #3). A second glass slide was applied to the waveguide to form a channel (as in example 1). Synthetic single stranded DNA containing a biotin at the 3' end and either fluorescein, adamantane or quinoline at the 5' end was diluted 3 µl into 50 µl of 1% casein, 10 mM Tris, pH 7.4, 15 mM NaCl. The final DNA concentrations were approximately 100 nM. The DNA sequences are shown in Table 9.1.

TABLE 9.1

| SEQ ID No. | Sequence 5'                                          3' |
|---|---|
| 19 | biotin-GGACACGGACACGGACACGGACAC-fluorescein |
| 20 | biotin-GGACACGGACACGGACACGGACAC-quinoline |
| 21 | biotin-GGACACGGACACGGACACGGACAC-adamantane |

Figure 12B:
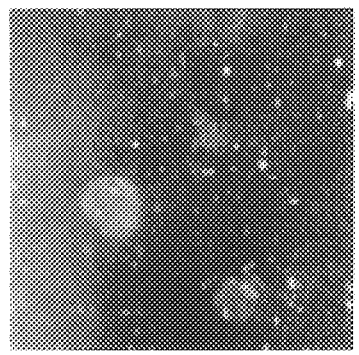
Figure 12D:
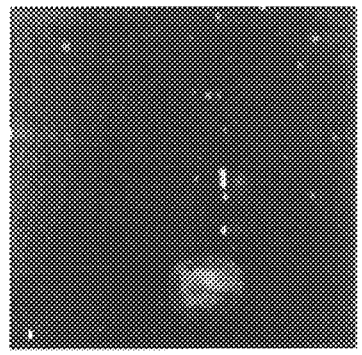
Figure 12C:
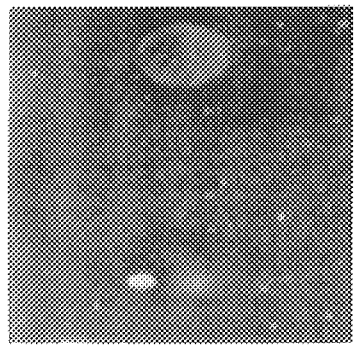
Figure 12E:
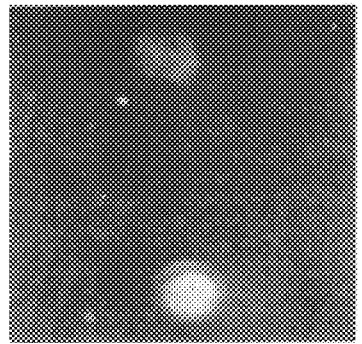

The resulting solutions were mixed with equal volumes of anti-biotin selenium conjugate (example 4) and introduced to the waveguide channel by capillary action. FIGS. 12b to 12d show the results using DNA solutions containing a single labeled species. SEQ ID No. 21 is used in FIG. 12b, SEQ ID No. 19 is used in FIG. 12c, and SEQ ID No. 20 is used in FIG. 12d. In figure 12e, a mixture of quinoline-biotin DNA and fluorescein-biotin DNA resulted in detectable signals at the two appropriate capture sites (spots 1 and 3). Hence, the waveguide system allowed for simultaneous detection of multiple analytes in a mixture.

The above example describe several specific embodiments of the invention but the invention is not restricted to these specific examples. Rather, the invention to be protected is defined by the appended claims.

We claim:

1. A method for determining base differences between at least two nucleic acid sequences, the method comprising:

(a) providing a waveguide device, the waveguide device comprising (i) a transparent element having a refractive index greater than that of the fluid sample; (ii) a light receiving edge; and (iii) a reactive surface comprising a plurality of sites having oligonucleotide immobilized thereon, said sites defining an array of oligonucleotides, said reactive surface further comprising other non-situs portions having no oligonucleotides immobilized thereon;

(b) contacting the reactive surface under hybridizing conditions with said at least two nucleic acid sequences wherein said nucleic acid sequences, either directly or through intermediate cognate binding pairs, is labeled with a light scattering label; thereby forming light scattering label complexes attached at those sites of the reactive surface having an oligonucleotide complementary to said nucleic acid sequences immobilized thereon;

(c) illuminating the light receiving edge of the waveguide with light effective to create total internal reflection within the waveguide, thereby simultaneously illuminating the entire reactive surface;

(d) collecting light scattered across the entire reactive surface by said light scattering label;

(e) comparing the degree of light scattering at each situs with either (i) the degree of light scattering at a non-situs portion; or (ii) the degree of light scattering at another situs;

(f) incrementally increasing the stringency conditions at the reactive surface of the waveguide device to initiate dissociation of bound nucleic acid from the sites wherein said comparing of step (e) is continued during the incremental stringency increase;

whereby base differences between the at least two oligonucleotides can be distinguished by differences in dissociation properties.

2. The method of claim 1 wherein stringency conditions are increased incrementally by continuously increasing the temperature.

* * * * *